United States Patent [19]
Cohen et al.

[11] Patent Number: 5,849,695
[45] Date of Patent: Dec. 15, 1998

[54] PARATHYROID HORMONE ANALOGUES USEFUL FOR TREATMENT OF OSTEOPOROSIS AND DISORDERS OF CALCIUM MEATABOLISM IN MAMMALS

[75] Inventors: Fred E. Cohen, San Francisco; Robert A. Nissenson, Burlingame; Gordon J. Strewler, San Francisco, all of Calif.

[73] Assignee: The Regents of the University of California, Oakland, Calif.

[21] Appl. No.: 972,466

[22] Filed: Jan. 13, 1993

Related U.S. Application Data

[63] Continuation-in-part of Ser. No. 553,760, Jul. 13, 1993, abandoned.

[51] Int. Cl.$^6$ .......................... A61K 38/29; A61K 38/04
[52] U.S. Cl. .......................... 514/12; 530/307; 530/324; 530/399
[58] Field of Search ..................... 530/307, 324, 530/399; 574/12; 930/21, 60

[56] References Cited

U.S. PATENT DOCUMENTS

| | | | |
|---|---|---|---|
| 3,886,132 | 5/1975 | Brewer et al. | 530/307 |
| 4,771,124 | 9/1988 | Rosenblatt et al. | 530/324 |
| 4,968,669 | 11/1990 | Rosenblatt et al. | 514/12 |
| 5,001,223 | 3/1991 | Rosenblatt et al. | 530/324 |
| 5,093,233 | 3/1992 | Rosenblatt et al. | 530/324 |

OTHER PUBLICATIONS

Schulz et al, *Principles of Protein Structure*, pp. 14–16, Springer–Verlag (NY), 1979.
Chorev et al, pp. 621–626 in *Peptide Chemistry 1987*, edited by Shiba et al. (Protein Res. Found., Osaka) 1988.

*Primary Examiner*—David L. Fitzgerald
*Assistant Examiner*—Elizabeth C. Kemmerer
*Attorney, Agent, or Firm*—Peters, Verny, Jones & Biksa, L.L.P.

[57] ABSTRACT

The present invention relates polypeptide analogs which have agonist or antagonist or tissue selection properties relative to parathyroid hormone (PTH), parathyroid hormone-like protein (PLP) or parathyroid-related protein (PTHrP). The serine amino acid at position 3, the glutamine amino acid at position 6, the histidine amino acid at position 9 or combinations thereof are substituted by other natural or synthetic amino acids. Preferably, a human PTH fragment of about 34 amino acids is sufficient for pharmacological activity. These polypeptides are useful as agonists or antagonists in the treatment of a human being for disease conditions of cancer, osteoporosis, hypercalcemia, or hyperparathyroid disease conditions. The invention also concerns a method of performing certain assays using the modified peptides, and based on the results of the assays falling within preset limits, selecting those modified peptides which shall be useful in the treatment of disease conditions.

29 Claims, 12 Drawing Sheets

| | 1 | | | | 5 | | | | | 10 | | | | | 15 | | | | | 20 | | | | | 25 | | | | | 30 | | | | |
|---|---|---|---|---|---|---|---|---|---|---|---|---|---|---|---|---|---|---|---|---|---|---|---|---|---|---|---|---|---|---|---|---|---|---|
| PTH bovine | A | V | S | E | I | Q | F | M | H | N | L | G | K | H | L | S | S | M | E | R | V | E | W | L | R | K | K | L | Q | D | V | H | N | F |
| PTH human | S | V | S | E | I | Q | L | M | H | N | L | G | K | H | L | N | S | M | E | R | V | E | W | L | R | K | K | L | Q | D | V | H | N | F |
| PTH rat | A | V | S | E | I | Q | L | M | H | N | L | G | K | H | L | A | S | V | E | R | M | Q | W | L | R | K | K | L | Q | D | V | H | N | F |
| PTH chicken | S | V | S | E | M | Q | L | M | H | N | L | G | E | H | R | H | T | V | E | R | Q | D | W | L | Q | M | K | L | Q | D | V | H | S | A |
| PTH porcine | S | V | S | E | I | Q | L | M | H | N | L | G | K | H | L | S | S | L | E | R | V | E | W | L | R | K | K | L | Q | D | V | H | N | F |
| PTHrP human | A | V | S | E | H | Q | L | L | H | D | K | G | K | S | I | Q | D | L | R | R | R | F | F | L | H | H | L | I | A | E | I | H | T | A |
| PTHrP chicken | A | V | S | E | H | Q | L | L | H | D | K | G | K | S | I | Q | D | L | R | R | R | I | F | L | Q | N | L | I | E | G | V | N | T | A |

FIG._1
(PRIOR ART)

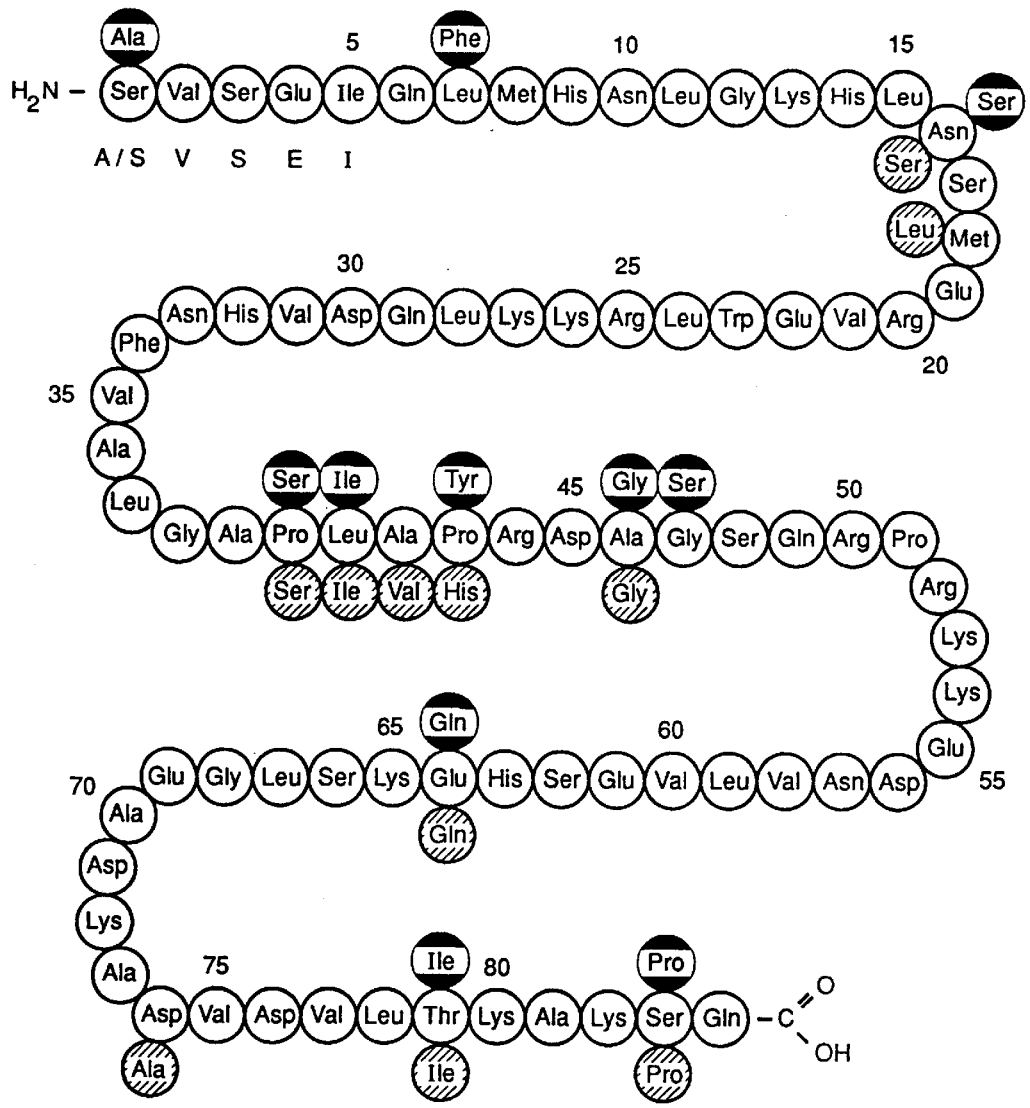
FIG._1A
(PRIOR ART)

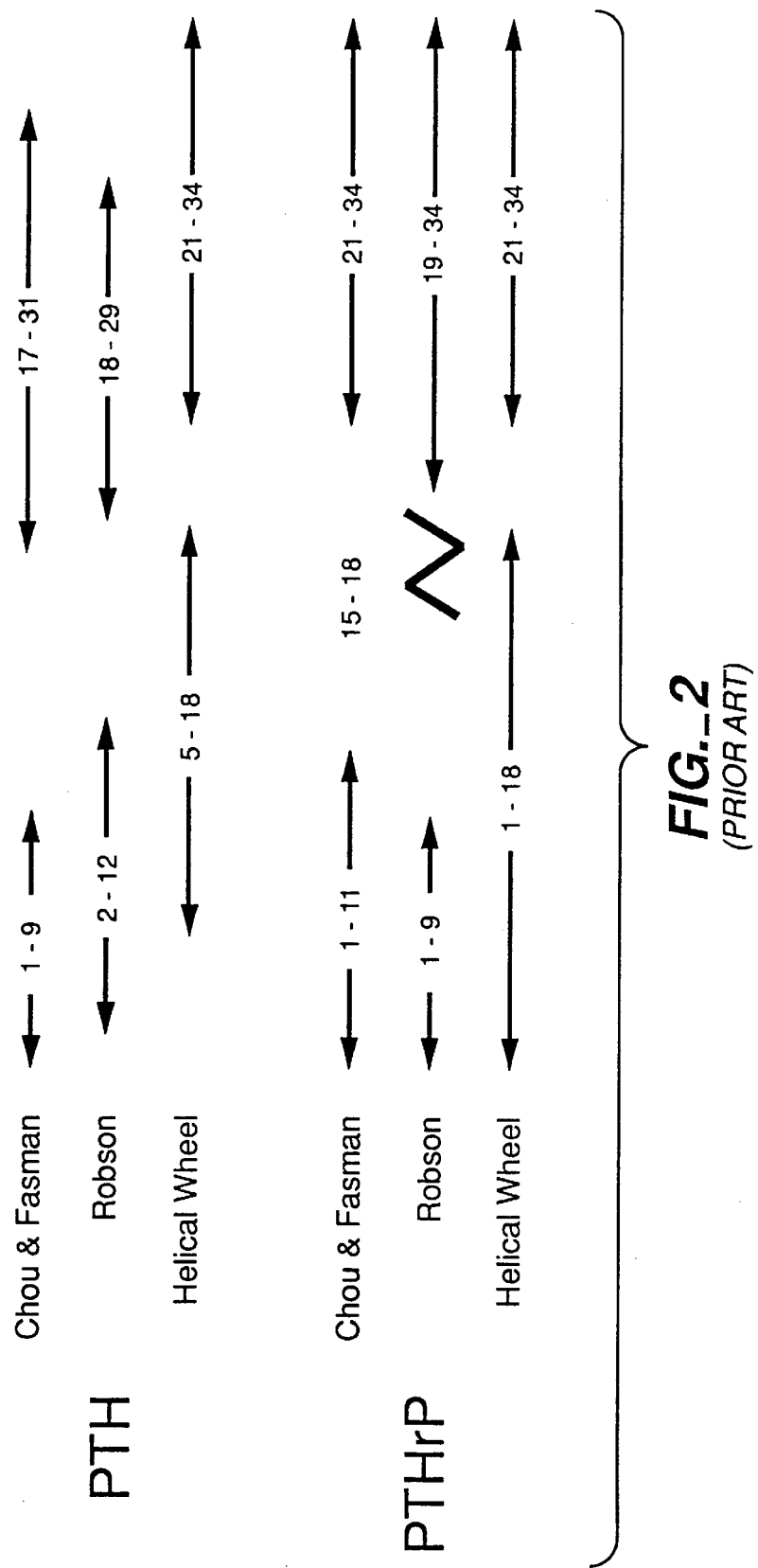
FIG._2 (PRIOR ART)

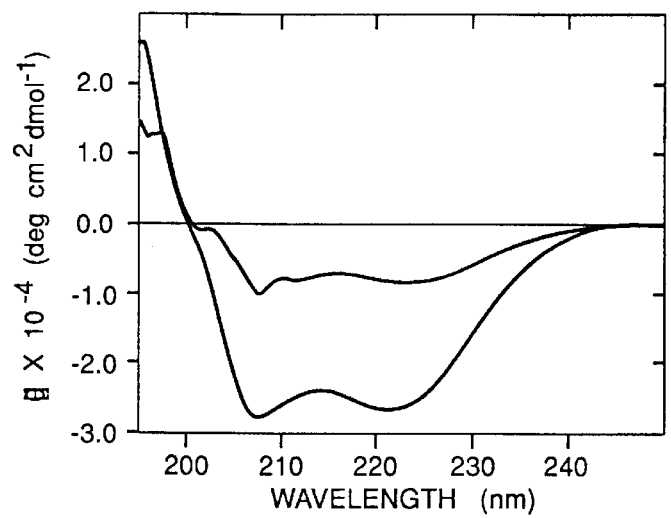
FIG._3A
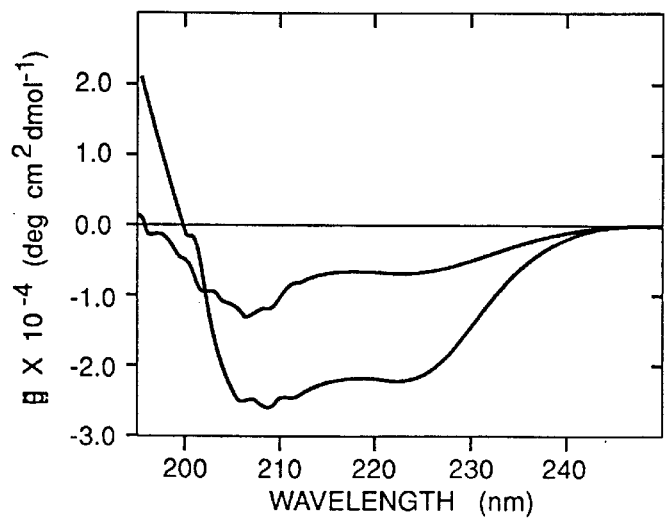
FIG._3B
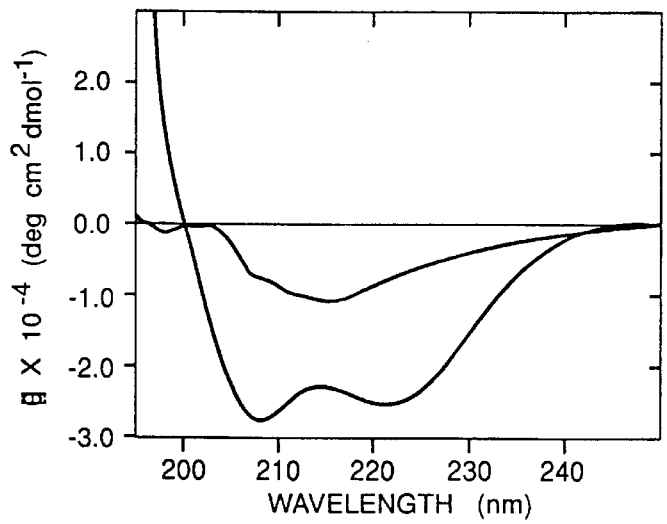
FIG._3C

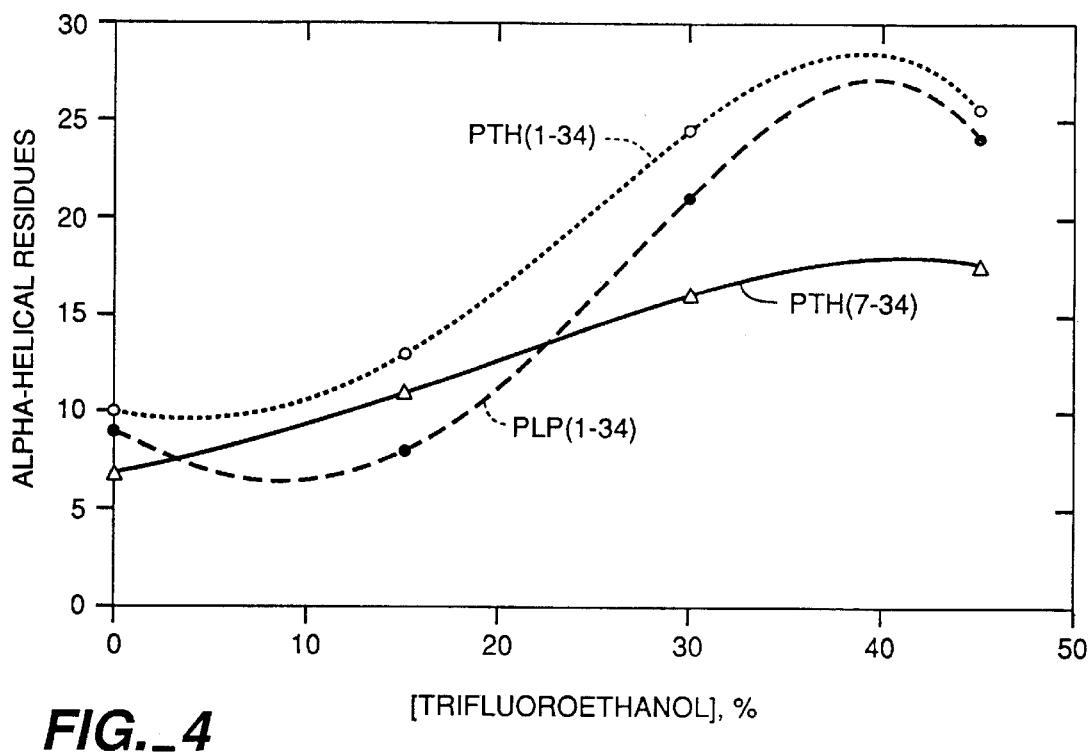
FIG._4
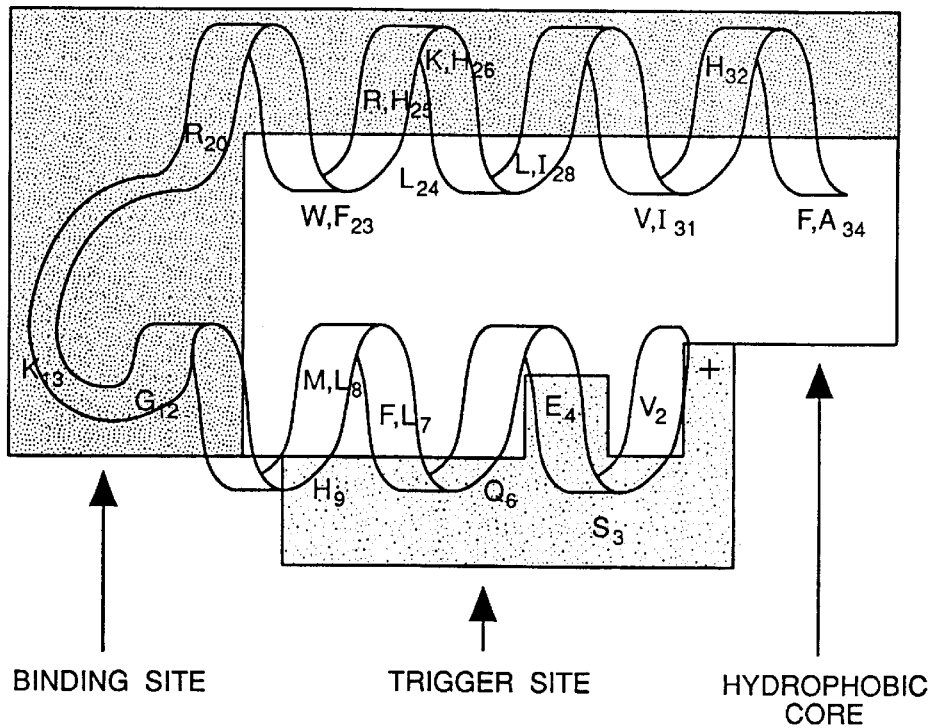
FIG._5

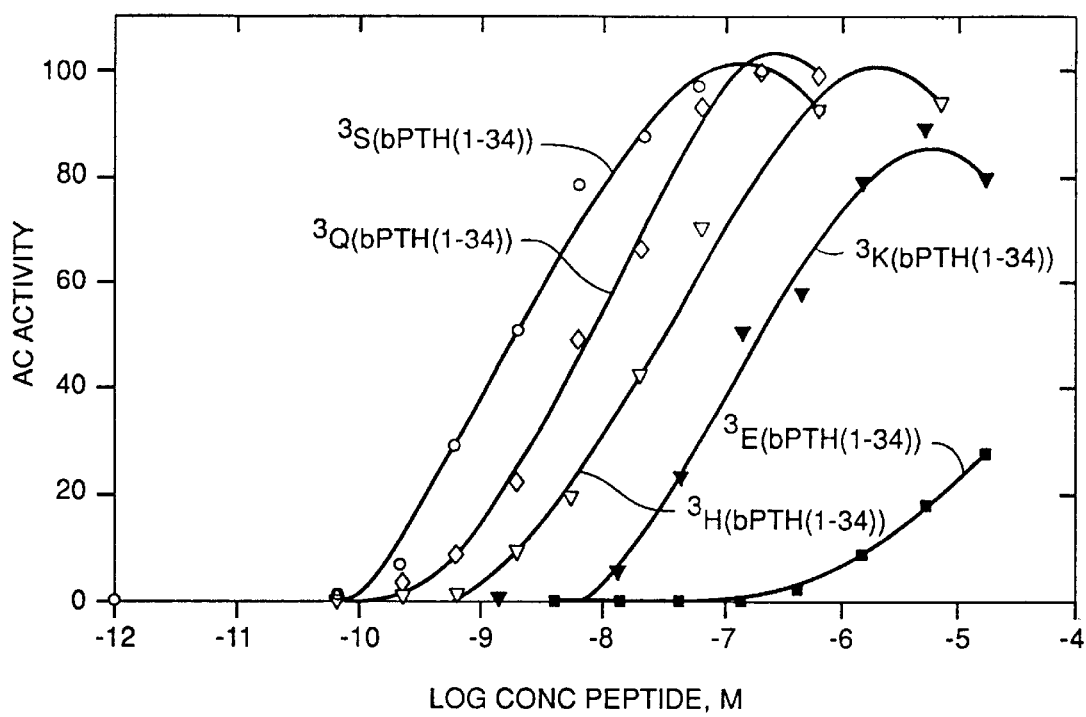
FIG._6A
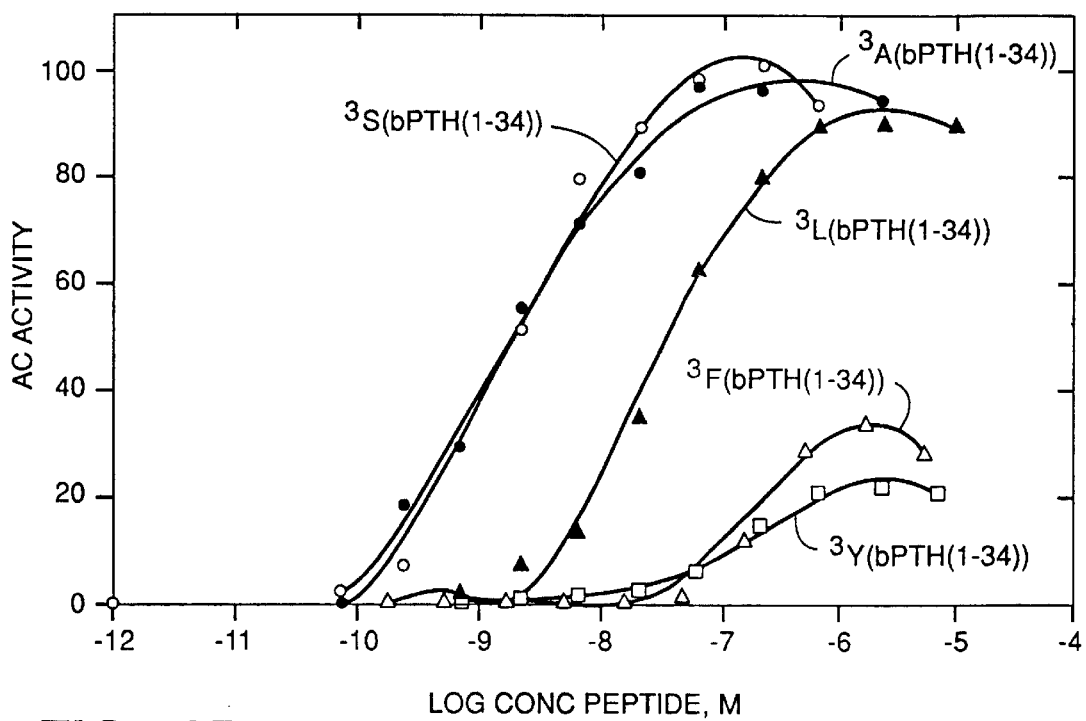
FIG._6B

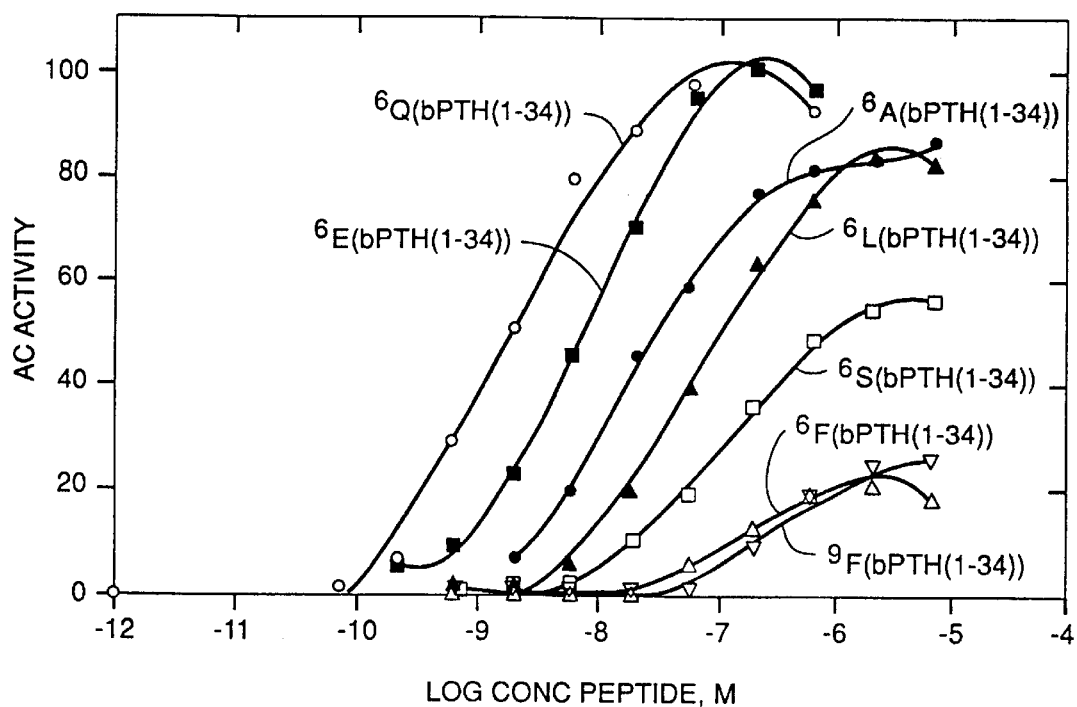
FIG._6C
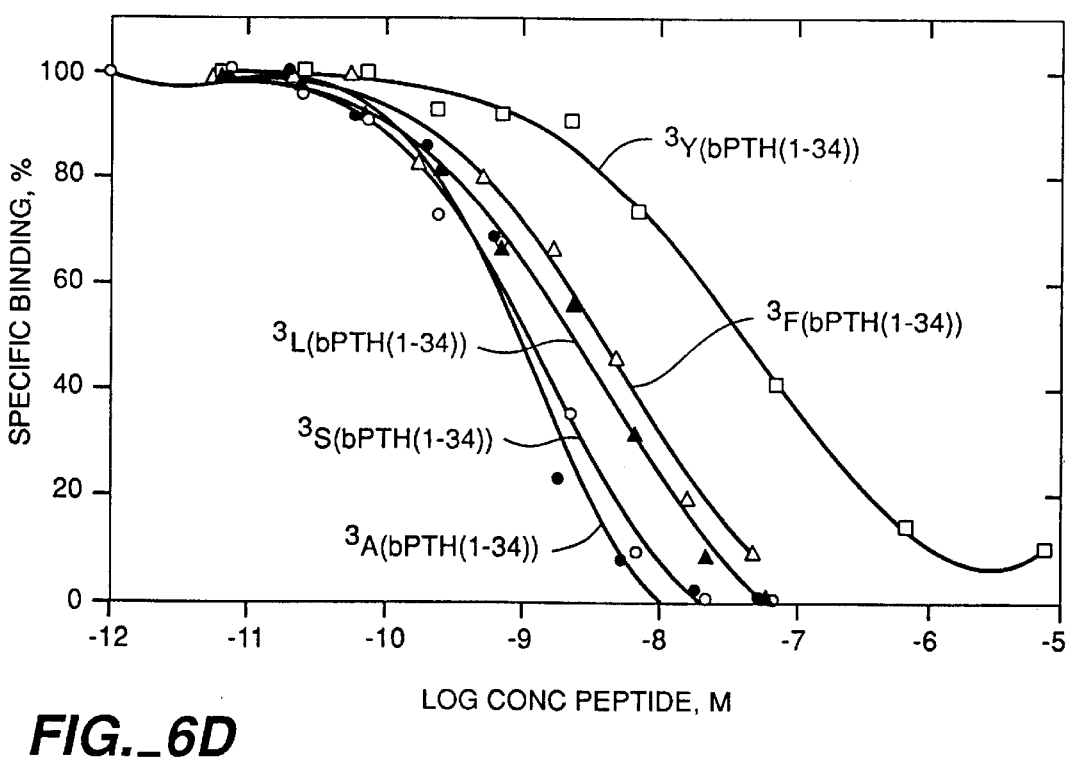
FIG._6D

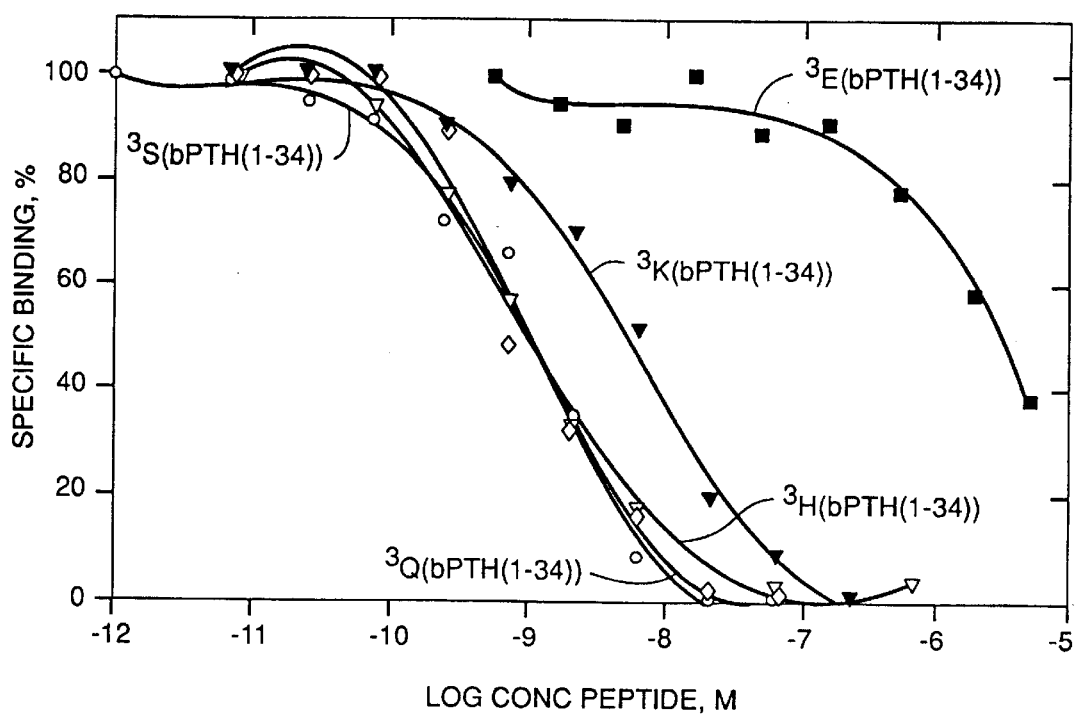
FIG._6E
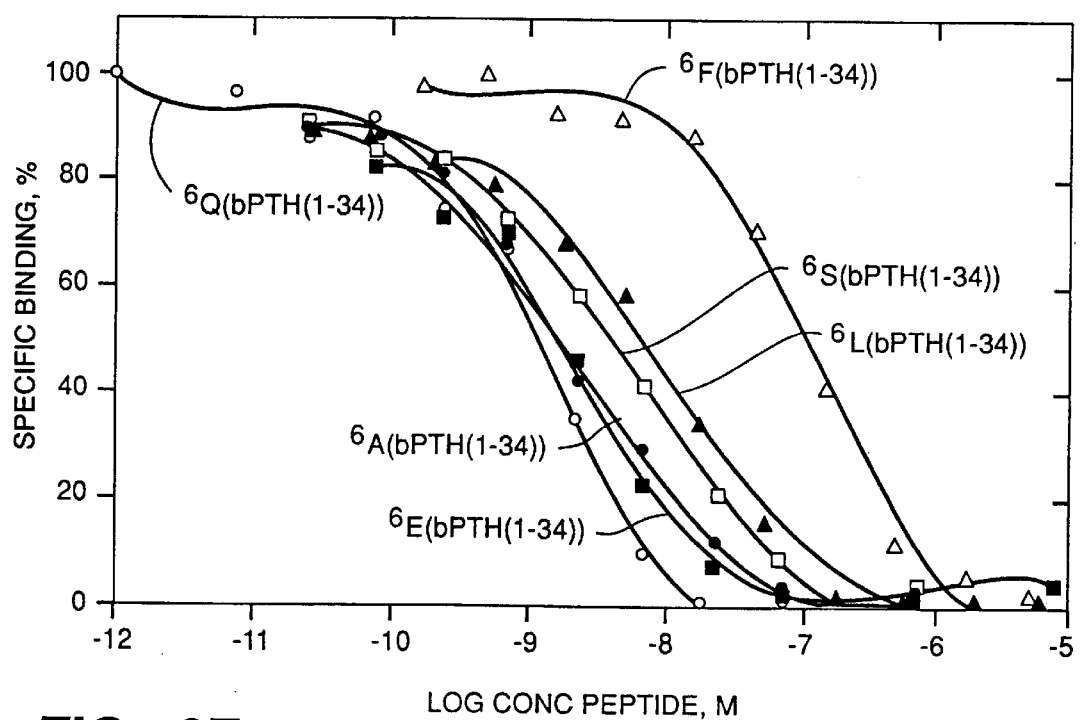
FIG._6F

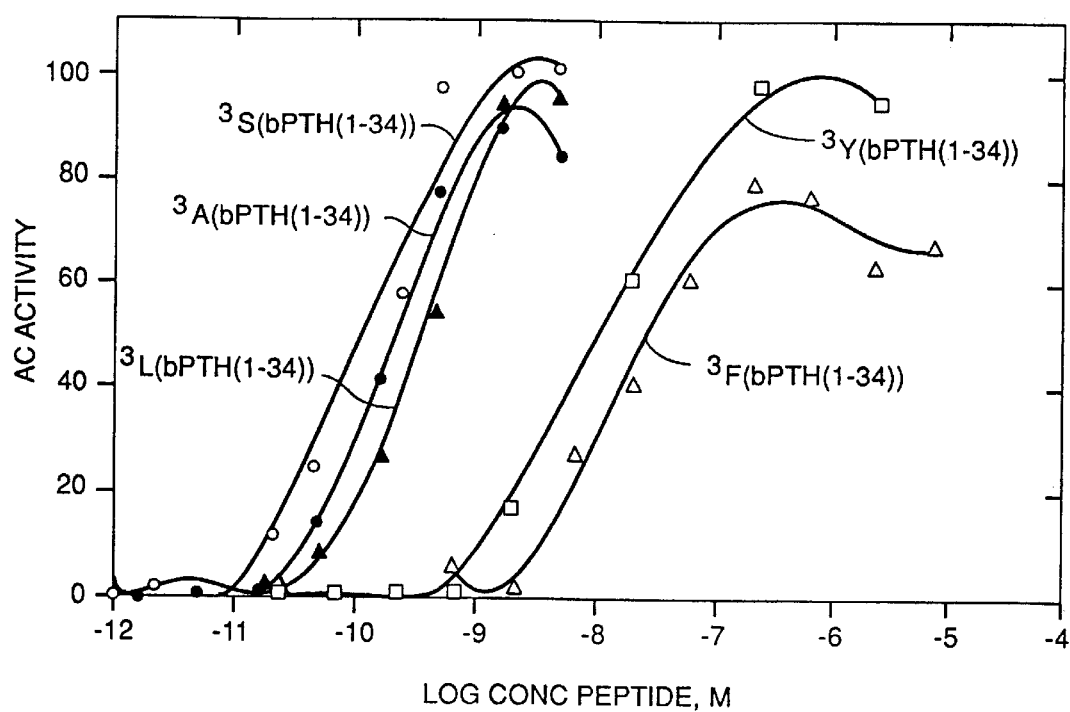
FIG._7A
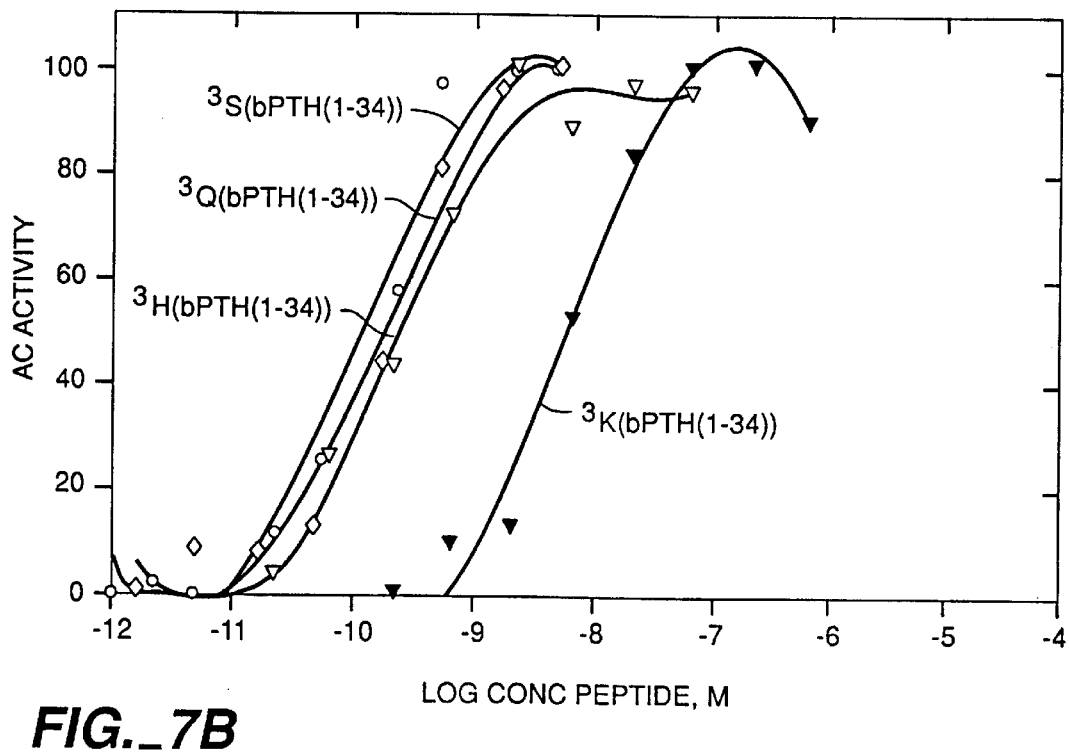
FIG._7B

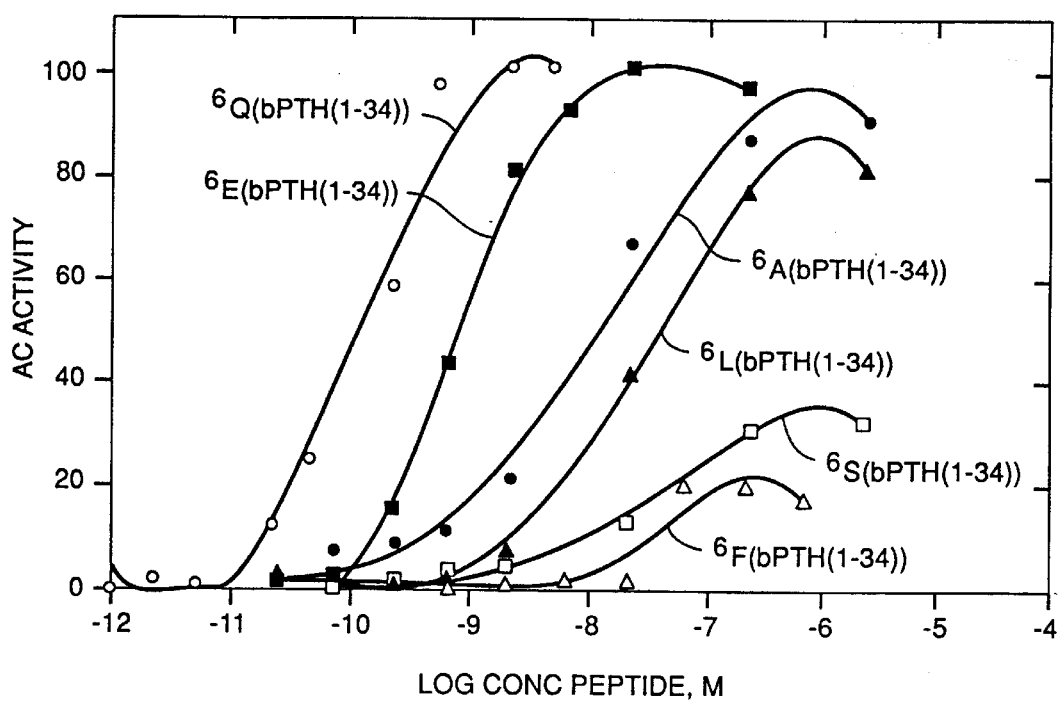
FIG._7C
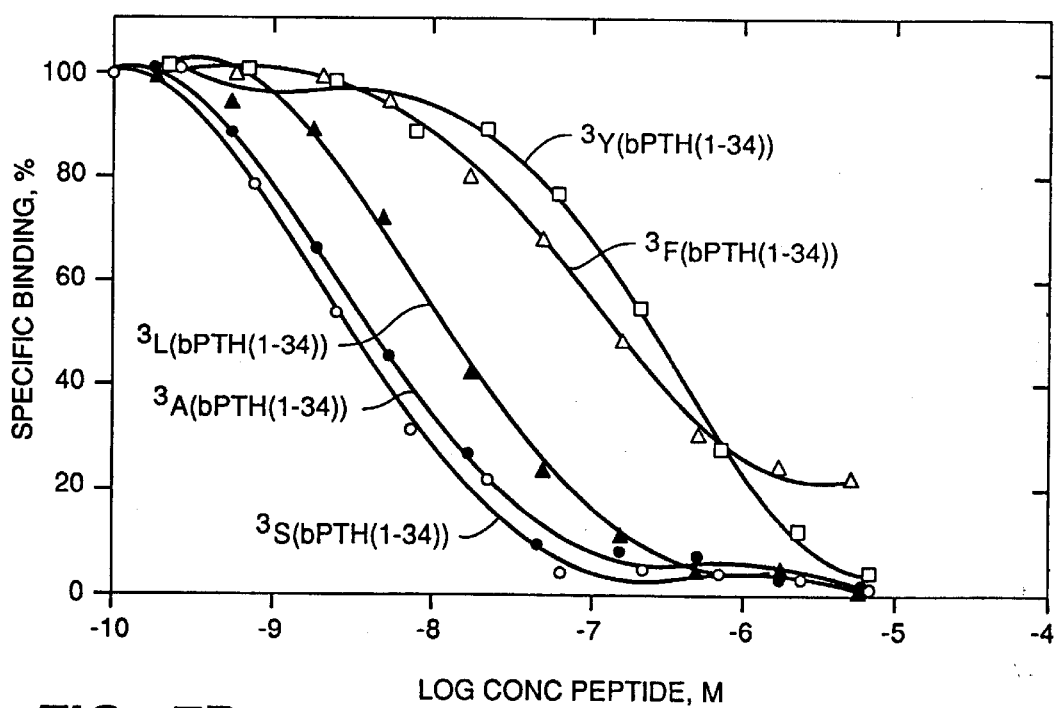
FIG._7D

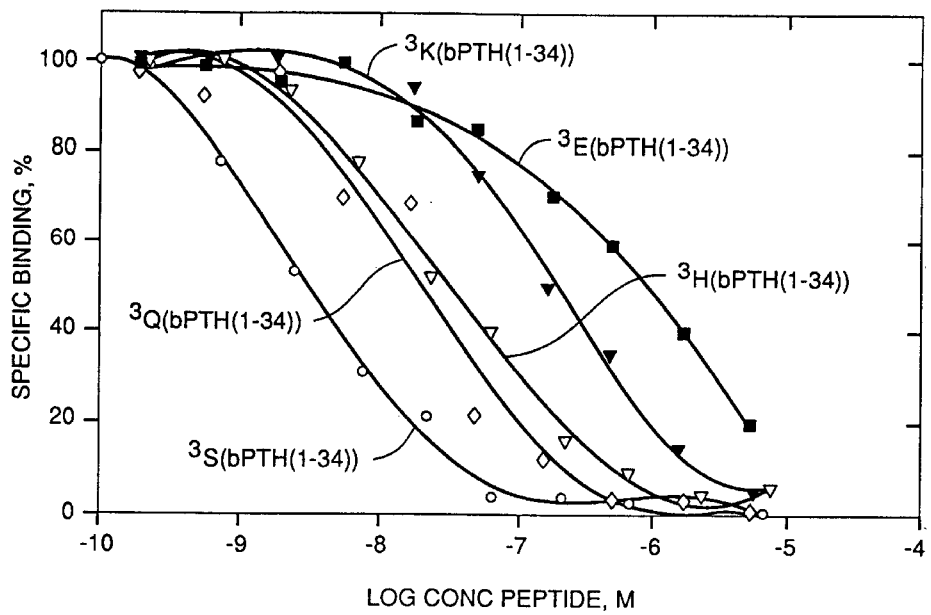
FIG._7E
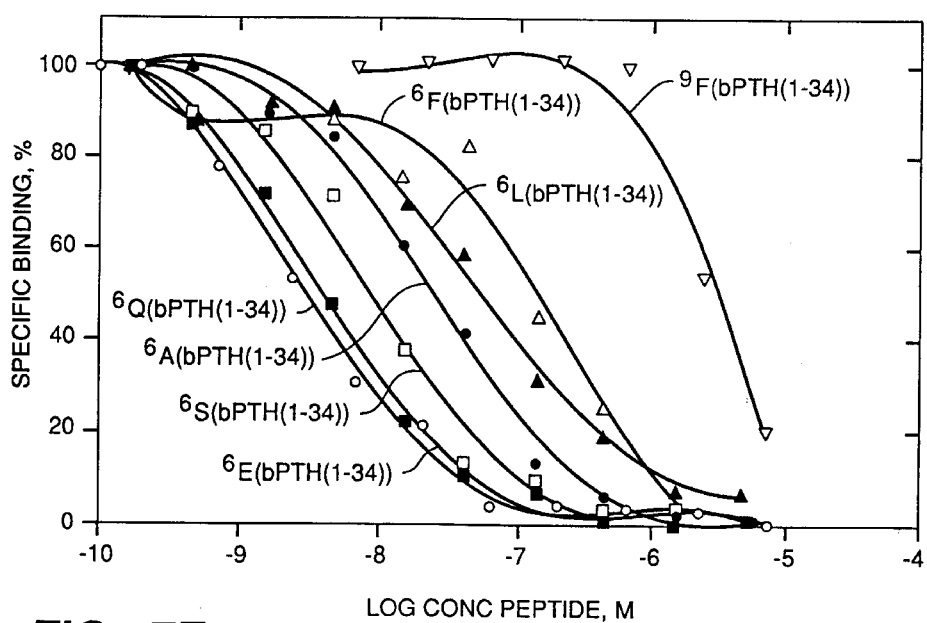
FIG._7F

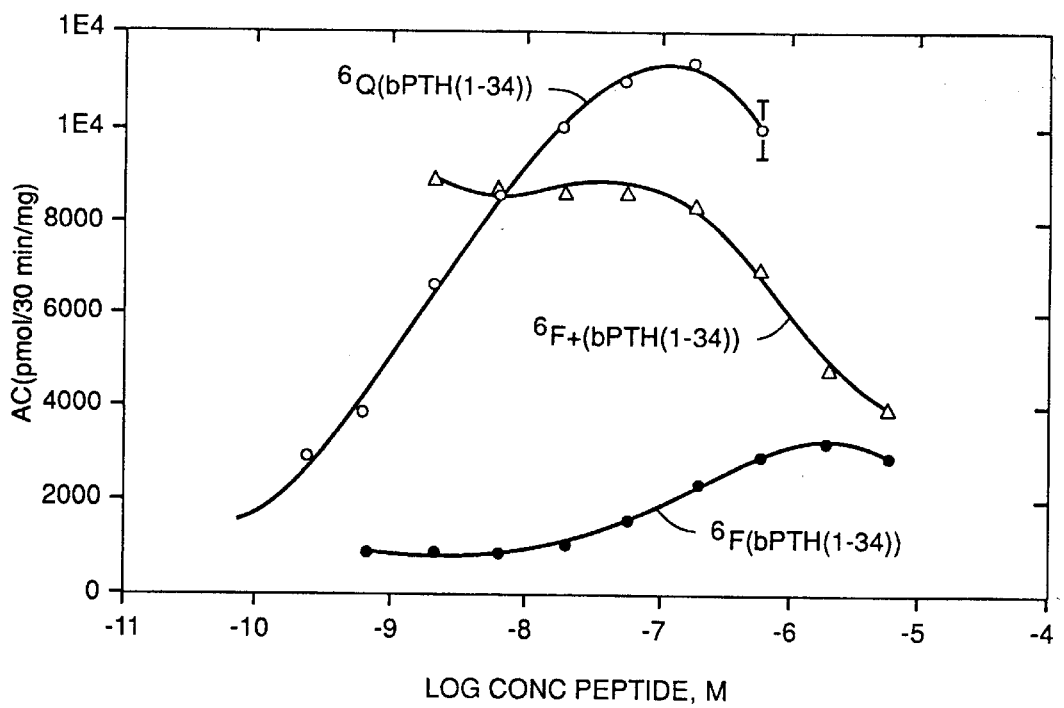
FIG._8A
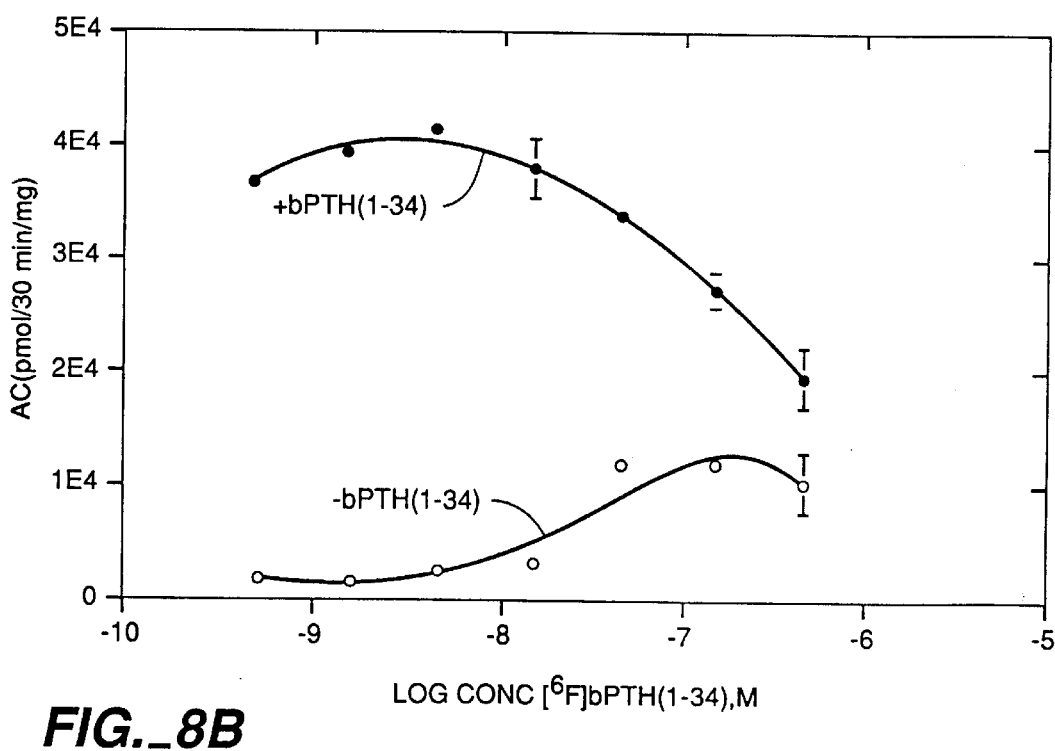
FIG._8B

PARATHYROID HORMONE ANALOGUES USEFUL FOR TREATMENT OF OSTEOPOROSIS AND DISORDERS OF CALCIUM MEATABOLISM IN MAMMALS

RELATED APPLICATIONS

The present application is a continuation-in-part of Ser. No. 553,760 filed Jul. 13, 1990, now abandoned, which is incorporated herein by reference.

ORIGIN OF THE INVENTION

The research disclosed herein was supported in part by the U.S. National Institutes of Health Grants Nos: GM 39900, CA 34738, and AM 35323, and by the Research Service of the Veterans Administration. The U.S. Government has certain rights in this invention.

BACKGROUND OF THE INVENTION

1. Field of the Invention

The present invention relates to polypeptide analogs which have agonist or antagonist properties relative to parathyroid hormone, (PTH), parathyroid hormone-like protein (PLP) or parathyroid-related protein (PTHrP). The serine amino acid at position 3, the glutamine amino acid at position 6, or the histidine amino acid at position 9, or combinations thereof, are substituted by other natural or synthetic amino acids. Preferably, a human PTH fragment of about 34 amino acids is sufficient for useful pharmacological activity. These polypeptides are useful in the treatment of a human being for conditions of cancer, osteoporosis, hypercalcemia, or hyperparathyroid disease.

2. Description of Related Art

The search for potent PTH agonists and/or antagonists has been intensive. The availability of potent and specific antagonists would provide a powerful research tool for the study of the mechanism of action and physiological and/or pathological role for PTH. Some research efforts have resulted in in vitro PTH antagonists. However, during in vivo evaluation of these polypeptides, they often did not have any clear antagonist properties.

For a number of polypeptide hormones, discrete, localized structural modifications are sufficient to convert a receptor agonist to a competitive receptor antagonist. Underlying this observation is the idea that the distinct functions of receptor-binding of hormone and initiation of biologic action, are signalled by distinct structural domains within the polypeptide hormone sequence. Parathyroid hormone (PTH) is a well-studied example of such a polypeptide hormone. PTH (1–34) is a full agonist of the native 84 amino-acid hormone with respect to adenylate cyclase activation in canine renal membranes (See Ref. 1 below. The letters used are the conventional ones to describe an amino acid sequence). Amino-terminal truncation results in polypeptides that are competitive antagonists of PTH-stimulated adenylate cyclase. Thus [Tyr$^{34}$]bPTH(7–34)amide retains moderate affinity for renal PTH receptors, but does not have any agonist activity. Specific weak receptor binding activity is retained in a fragment as small as PTH(25–34) (Ref. 2). On the other hand, carboxyl-terminal truncations of PTH(1–34) produce agonists with progressively lower affinities. PTH (1–25) is reported to be essentially inactive (Ref. 3–5). The "receptor-binding domain" of PTH is believed to include amino acid residues 25–34 and the "activation domain" includes amino acid residues 1-6.

A recently identifed tumor-derived protein bears limited sequence identity with PTH (Ref. 6–8) and activates PTH-responsive adenylate cyclase with a potency comparable to that of PTH (Ref. 9–11). This 139–141 amino-acid PTH-related protein (PTHrP), and synthetic amino-terminal fragments derived therefrom, display high affinity for renal and skeletal PTH receptors (Ref. 12–15). They also reproduce the major biologic actions of PTH in vivo and in vitro (Ref. 12,15–18). PTH-related protein is found in a variety of human and animal tumors, and evidence suggests that the protein plays a pathogenetic role in the hypercalcemia that frequently accompanies malignant disease (Ref. 19,20). The amino acid sequence similarities between mammmalian PTHs and PTHrP are largely limited to the amino-terminal terminal 1–13 residues, of which 8 are identical, See FIG. 1. Although PTHrP displays a high affinity for PTH receptors, only 1 of 10 amino acids in the 25–34 receptor-binding domain of PTH is common to PTHrP. Furthermore, a polypeptide analogue of PTHrP(14–38) is reported to bind (with low affinity) to PTH receptors in ROS 17/2.8 rat osteosarcoma cells (Ref. 21). Thus, conformational similarity rather than a strict conservation of sequence may underlie this interaction of PTH and PTHrP with a common receptor.

T. Gardella, et al. (Sep. 12, 1989) *Bone and Mineral Research*, T. suppl., Abstract 642, is a brief report about a mutational analysis of human parathyroid hormone 1–84. Mutation for any of the first four amino acids was reported to decrease activity of PTH.

T. Gardella, et al. (Jun. 23, 1990) Program of the 72nd Annual Meeting of the Endocrine Society, Abstract 1071, briefly report on the design of novel PTH 1–84 analogs. Modifications at the number two and number four amino acids are cited in the abstract.

Some additional references of interest in this art include the following:

1. A. P. Teitelbaum, et al. (182) *Endocrinol.*, Vol. 111, 1524–1533.
2. M. Rosenblatt, et al. (1980) *Endocrinol.*, Vol. 107, 545–550.
3. G. V. Segre, et al. (1979) *J. Biol. Chem.*, Vol. 254, 6980–6996.
4. M. Rosenblatt (1982) in *Endocrinology of Calcium Metabolism*. ed. Parsons, J. A. (Raven Press, N.Y.) pp. 103–142.
5. G. W. Tregear, et al. (1973) *Endocrinol.*, Vol. 93, 1349–1353.
6. L. J. Suva, et al. (1987) *Science*, Vol. 237, 893–896.
7. M. Mangin, et al. (1988) *Proc. Nat. Acad. Sci. USA*, Vol. 85 597–601.
8. M. A. Thiede, et al. (1988) *Proc. Natl. Acad. Sci USA*, Vol. 85, 4605–4609.
9. W. J. Burtis, et al. (1987) *J. Biol. Chem.*, Vol. 262, 7151–7156.
10. J. M. Moseley, et al. (1987) *Proc. Natl. Acad. Sci. USA*, Vol. 84, 5048–5052.
11. G. J. Strewler, et al. (1987) *J. Clin. Invest.*, Vol. 80 1803–1807.
12. N. Horiuchi, et al. (1987) *Science*, Vol. 238, 1566–1568.
13. H. Juppner, et al. (1988) *J. Biol. Chem.*, Vol. 263, 8557–8560.
14. R. A. Nissenson, et al. (1988) *J. Biol. Chem.*, Vol. 238, 1566–1568.
15. B. E. Kemp, (1987) *Science, Vol.* 238, 1568–1570.
16. A. F. Stewart, et al. (1988) *J. Clin. Invest.*, Vol. 81, 596–600.

17. A. J. P. Yates, et al. (1988) *J. Clin. Invest.*, Vol. 81, 932–938.
18. D. D. Thompson, et al (1988) *Proc. Natl. Acad. Sci. USA*, Vol. 85, 5673–5677.
19. A. A. Budayr, et al. (1989) *Ann. Int. Med.*, Vol. 111, 807–812.
20. J. E. Henderson, et al. (1990) *J. Bone Miner. Res.*, Vol. 5, 105–113.
21. A. B. Abou-Samra, et al. (1989) *Endocrinol.*, Vol. 125, 2215–2217.
22. P. Y. Chou, et al. (1974) *Biochemistry*, Vol. 12, 211–245.
23. J. R. Garnier, et al. (1978) *J. Mol. Biol.*, Vol. 120, 97–120.
24. E. T. Kaiser, et al. (1984) *Science*, Vol. 223, 249–255.
25. M. Schiffer, et al. (1967) *Biophys. J.*, Vol. 7, 121–135.
26. A. M. Fiskin, et al. (1977) *J. Biol. Chem.*, Vol. 252, 8261–8268.
27. J. E. Zull, et al. (1980) *Proc. Natl. Acad. Sci. USA*, Vol. 77, 3791–3795.
28. J. A. Barden, et al. (1989) *Eur. J. Biochem.*, Vol. 184, 379–394.
29. J. W. Taylor, et al. (1987) in *Methods In Enzymology*, eds. Wu. R. and Grossman, L. (Academic Press, Inc., San Diego, Calif.), Vol. 154, pp. 473–498.
30. J. M. Stewart, et al. (1972) in *Progress in Peptide Research*, ed Lande, S. (Gordon and Breach, Inc., New York, N.Y.), pp. 59–64.
31. R. J. Cotter (1988) *Anal. Chem.*, Vol. 60, 781A.
32. R. A. Nissenson, et al. (1985) in *Methods in Enzymology*, eds, Birnbaumer, L. and O'Malley, B.W. (Academic Press, Inc., Orlando, Fla.), Vol. 109, pp. 48–56.
33. A. P. Teitelbaum, et al, (1982) Endocrinol., Vol. 111, 1524-1533.
34. R. A. Nissenson, (1983) in *Assay of Calcium-regulating Hormones*, ed. Bikle, D. D. (Springer-Verlag, New York, N.Y.), 247–259.
35. S. D .H. Chan, et al. (1990) *Molec. Endocrinol.* Vol. 4, pp. 638–346.
36. Y. Salomon, et al. (1974) *Anal. Biochem.* Vol. 58, 541–548.
37. J. E. Zull, (1990) *J. Biol Chem.*, Vol. 265, 5671–5676.
38. G. V. Shah, et al. (1987) *Mol Cell Endocrinol.*, Vol. 49, 203–210.
39. B. S. Hong, et al. (1986) Peptides, Vol. 7, 1131–1135.
40. T. J. Richmond, et al. (1978) *J. Mol. Biol.*, Vol. 119, 537–555.
41. F. E. Cohen, et al. (1979) *J. Mol. Biol.*, Vol. 132, 275–288.
42. R. M. Epand, et al. (1985) *Int. J. Peptide Protein Res.*, Vol. 25, 594–600.
43. W. G. J. Hol, et al. (1978) *Nature*, Vol. 273, 443–446.
44. C. Chothia, et al. (1977) *Proc. Nat. Acad. Sci. USA*, Vol. 74, 4130–4134.
45. S. R. Presnell et al, (1989) *Proc. Nat. Acad. Sci.*, Vol. 86, 6592–6596.
46. I. Glover, et al. (1983) *Biopolymers*, Vol. 22, 293–304.
47. S. C. Lee, et al. (1989) *Biopolymers*, Vol. 28, 1115–1127.
48. J. M. Coddington, et al. (1989) *Molec. Endocrinol.* Vol. 3, 749–753.
49. A. L. Frelinger, III et al. (1984) *J. Biol. Chem.*, Vol. 259, 5507–5513.
50. R. A. Nissenson, et al. (1979) *J. Biol. Chem.*, Vol. 254, 1469–1475.
51. M. Rosenblatt, et al. (1976) *J. Biol. Chem.*, Vol. 251, 159–164.
52. M. Rosenblatt, et al. (1977) *Endocrin. Res. Commun.*, Vol. 4, 115–133.
53. M. W. Draper, et al. (1982) *J. Biol. Chem.*, Vol. 257, 3714–3718.
54. J. A. Parsons, et al. (1975) in *Calcium-regulating Hormones: Proceedings of the Fifth Parathyroid Conference*, eds. Talmage, R. V., Owen, M. and Parsons, J. A. (Excerpta Medica, Amsterdam), pp. 34–39.
55. J. E. Zull, et al. (1987) *Mol. Cell. Endocrinol.*, Vol. 51, 267–271.
56. C. D. Strader, et al. (1987) *Proc. Nat. Acad. Sci. USA*, Vol. 84, 4384–4388.
57. F. M. Richards, (1974) *J. Mol. Biol.*, Vol. 82, 1–14.
58. L. Corporale, (1988) in *Peptides: Structure and Function. Proceedings of the Ninth American Peptide Symposium*. eds. Deber, C. M., Hruby, V. J., and Kopple, K. D. pp. 663–666.
59. H. B. Brewer, et al., U.S. Pat. No. 3,886,132.
60. M. Rosenblatt, et al., U.S. Pat. No. 4,771,124.
61. G. E. Schulz, et al., *Principles of Protien Structure*, Springer Verlag, New York, N.Y. ISBN 0387-903348 (1979).
62. H. T. Keutmann, et al. (1985), *Endocrinology*, Vol. 117(3), p. 1230.

All references, articles, patents, standards, etc. cited at any point in this application are incorporated herein by reference in their entirety.

Reference numbers in parenthesis in the text are to the numbers of the references found in this section.

At the present time a number of PTH analogs and studies have been reported for replacement of amino acids primarily the 10–34 region of the polypeptide chain. However, few hPTH or bPTH, etc. analogs have been reported where the amino acids are substituted in the 1–9 amino acid positions. The present invention provides a method to select and to produce novel hPTH or bPTH, etc. analogs where the amino acids at positions 3 and/or 6 and/or 9 have been replaced using the natural or synthetically made unnatural (unusual) amino acids. These analogues replaced at the 3, 6, or 9 positions have surface side chains which are useful to modulate receptor binding and activity. These analogues are useful as agonists or antagonists in the treatment of a number of disease conditions, particularly osteoporosis.

SUMMARY OF THE INVENTION

In one aspect, the present invention concerns a pharmaceutical composition comprising a compound of the formula:

$H_2N$-(Ser or Ala)$^1$-Val-B$^3$-Glu-Ile-J$^6$-(Leu or Phe)$^7$-Met-X$^9$-Asn$^{10}$-Leu-Gly-Lys-His-Leu-(Asn or Ser)$^{16}$-Ser-(Met or Leu)$^{18}$—Glu-Arg$^{20}$-Val-Glu-Trp'Leu-Arg'Lys-Lys-Leu-Gln-Asp$^{30}$-Val-His—Asn-Phe$^{34}$-Z (Structure I), or the pharmaceutically acceptable salts thereof, wherein:
the amino acid B at position 3 is independently selected from L-serine or those other natural or synthetic D or L amino acids having a spatial volume comparable to or greater than serine, with the proviso that B is not glycine, the amino acid R at position 6 is independently selected from L-glutamine or from other natural or synthetic D or L amino acids or mixtures of the D and L amino acids, the amino acid X at position 9 is independently selected from L-histidine or other natural or synthetic D or L-amino acids, with the proviso that when group B is L-serine and group J is L-glutamine, Group X is not histidine, when group B is L-serine and group X is histidine, J is not glutamine, and when group J is glutamine and group X is histidine, group B is not L-serine, and Z is independently selected from -COOH, -COO-+M wherein M+ is selected from pharmacologically compatible cations, -(C=O)NH$_2$, or the sequence of amino acids of human parathyroid hormone, or of human parathyroid hormone-related protein.

In a preferred embodiment the amino acid at position 1 is serine, the amino acid at position 7 is leucine, the amino acid at position 16 is Asn, and the amino acid at position 18 is methionine, i.e. a modified analog of human PTH.

In a preferred embodiment, the amino acid at position 1 is alanine, the amino acid at position 7 is phenylalanine, the amino acid at position 16 is serine, and the amino acid at position 18 is methionine, i.e. a modified analog of bovine PTH.

In other preferred embodiments, Z, B or J are independently selected as follows:

Z is —COOH or —COO—M+ or —(C=O)NH$_2$;

B is a synthetic amino acid;

B is a naturally occurring amino acid;

J is a synthetic amino acid;

J is a naturally occurring amino acid;

B is L-serine and J is selected from Leu, Phe, Ala, Glu, Ser or Phe; or

J is L-glutamine and B is independently selected from Ala, Phe, Gln, Glu, Lys, His, Leu, or Tyr.

In another aspect, the invention also relates to a compound of wherein J is independently selected from L-Serine, Ala, Phe, Gln, Glu, Lys, His or Tyr.

In yet another aspect, J is independently selected from L-glutamine, Leu, Phe, Ala, Glu, Ser or Phe.

In another aspect, the present invention also relates to a pharmaceutical composition comprising a compound of structure I or a pharmaceutically acceptable salt thereof in admixture with a pharmaceutically acceptable excipient.

In another aspect, the present invention relates to pharmaceutical compositions comprising a compound of the structure for hPTH(1–34) wherein Z is selected —COOH or COO—+M or —(C=O)NH$_2$ (preferably the amide), in admixture, with a pharmaceutically acceptable excipient.

In another aspect, the invention also relates to a method of treatment of a mammal in need of therapeutic treatment, which method comprises administration of a therapeutically effective amount of the peptide analog of a compound of Structure I or a pharmaceutically acceptable salt thereof in admixture with a pharmaceutically acceptable excipient.

In another aspect, the invention also relates to administration of a therapeutically effective amount of a compound of structure I by oral, parenteral, subcutaneous, intramuscular, intravenous, vaginal, rectal, buccal, sublingual or intranasal means.

In another aspect, the invention also relates to a method of therapeutic treatment, wherein the compound of structure I is used to treat cancer, osteoporosis, hypercalcemia or hyperparathyroid conditions in a human being.

In another aspect, the present invention relates to a method for selecting polypeptide sequences modified at the 3, 6, 9 position or combinations thereof of a PTH or PTH(1–34) useful in pharmaceutical compositions, which method comprises:

(a) preparing an amino acid sequence of hPTH, bPTH, pPTH, hPTHrP, bPTHrP, hPTH(1–34), bPTH(1–34) or pPTH(1–34) wherein the amino acid at the 3, 6, 9 position or combinations thereof, are replaced by different D- or L-natural amino acids or unnatural amino acids;

(b) performing an assay using specific soft tissues, membranes, or cells to evaluate receptor binding and activity;

(c) performing an assay using specific bone cells to evaluate receptor binding and activity;

(d) (i) independently selecting those peptide amino acid analogs for further evaluation, having a high binding and high activity in the specific soft tissues, membranes or cells and a high specific bone cell binding and high activity, as agonists for medical treatment for disease conditions of the soft tissues, membranes, cells or bone, or alternatively;

(ii) independently selecting those peptide amino acid analogs for further evaluation, having a high binding and high activity as agonists in the specific soft tissues, membranes, or cells and a low specific bone cell binding and low activity as agonists for disease conditions of the soft tissues, membranes, or cells, or alternatively;

(iii) independently selecting those peptides for further evaluation as agonists having a low binding and low activity in specific tissues, membranes or cells, and high specific bone cell binding and high activity for disease conditions of the bone, or alternatively;

(iv) independently selecting high binding and low activity in tissues, membranes or cells and in bone cells for use as antagonists in the medical treatment of hormonal disorders and cancers; and (e) performing subsequent different assays or toxicity determinations on the amino acid analogs pursuant to identifying a useful pharmaceutical.

BRIEF DESCRIPTION OF THE DRAWINGS

FIG. 1 is a representation of aligned sequences of PTH (1–34) from five species of mammals and human and chicken PTHrP(1–34). Positions of sequence identity are highlighted with solid lines.

FIG. 1A is representation of the 1–84 amino acids of human PTH, bovine PTH and porcine PTH.

FIG. 2 is a representation of secondary-structural features of the 1–34 peptides of bPTH(1–34) and human PTHrP (1–34) as predicted by statistical and pattern-based theoretical approaches. The arrows indicate predicted alpha-helical structure, and the wavy line represents a possible beta-turn.

FIG. 3A–C are the circular dichroism (CD) spectra of peptides in the presence and absence of 45% trifluoroethanol. Nadirs at 208 nm and 222 nm are characteristic of a-helical structure. The peptides analyzed are: FIG. 3A, bPTH(1–34); FIG. 3B [Tyr$^{34}$]bPTH(7–34)amide; and FIG. 3C, hPTHrP(1–34)amide.

FIG. 4 is a representation of the effect of trifluoroethanol on the alpha-helical content of bPTH(1–34) (o), [Tyr$^{34}$] bPTH(7–34)amide (Δ), and hPLP(1–34)amide (•). The alpha-helical content was determined by deconvolution of circular dichroism spectra as described by Taylor and Kaiser (Ref. 29).

FIG. 5 is a schematic representation of the paired helix model for bPTH(1–34) and hPTHrP(1–34). Positions of relative sequence conservation are shown. The hydrophobic core, binding region, and trigger region are designated.

FIG. 6A–F, show graphs of the biologic activity in canine renal plasma membranes of analogues of PTH(1–34) containing substitutions at positions 3,6, and 9.

FIG. 6A shows adenylate cyclase (AC) activation produced by bPTH(1–34) (•), and [Glu$^3$]bPTH(1–34) (■), [His$^3$]bPTH(1–34) (▽), [Lys$^3$]bPTH(1–34) (▼), and [Gln$^3$]bPTH (1–34) (◇).

FIG. 6B shows adenylate cyclase (AC) activation produced by bPTH(1–34) (o), [Ala$^3$]bPTH(1–34) (●), [Phe$^3$]bPTH(1–34) (Δ), [Leu$^3$]bPTH(1–34) (▲), and [Tyr$^3$]bPTH (1–34) (□)

FIG. 6C shows adenylate cyclase activation produced by bPTH(1–34) (o), [Ala$^6$]bPTH(1–34) (●), [Phe$^6$]bPTH (1–34) (Δ) [Leu$^6$]bPTH(1–34) (▲), [Ser$^6$]bPTH(1–34) (□), [Glu$^6$]bPTH(1–34) (■), and [Phe$^6$]bPTH(1–34) (▽).

FIG. 6D shows competitive binding to PTH receptors by bPTH(1–34) (o), [Ala$^3$]bPTH(1–34) (●), [Phe$^3$]bPTH (1–34) (Δ), [Leu$^3$]bPTH(1–34) (▲), and [Tyr3]bPTH(1–34) (□).

FIG. 6E shows competitive binding to PTH receptors by bPTH(1–34) (o), [Glu$^3$]bPTH(1–34) (■), [His$^3$]bPTH (1–34) (▽), [Lys$^3$]bPTH(1–34) (▼), and [Gln$^3$]bPTH(1–34) (◇).

FIG. 6F shows competitive binding to PTH receptors by bPTH(1–34) (o), [Ala$^6$]bPTH(1–34) (●), [Phe$^6$]bPTH (1–34) (Δ), [Leu$^6$]bPTH(1–34) (▲), [Ser$^6$]bPTH(1–34) (□), and [Glu$^6$]bPTH(1–34) (■).

FIGS. 7A–F show graphs of the biologic activity in UMR 106-H5 cells of analogues of PTH(1–34) containing substitutions at positions 3, 6, and 9.

FIG. 7A shows adenylate cyclase (AC) activations produced by bPTH(1–34) (o), [Ala$^3$]bPTH(1–34) (●), [Phe$^3$]bPTH(1–34) (δ), [Leu$^3$]bPTH(1–34) (▲), and [Tyr$^3$]bPTH(1–34) (□).

FIG. 7B shows adenylate cyclase (AC) activation produced by bPTH(1–34) (o), [His3]bPTH(1–34) (▽), [Lys$^3$]bPTH(1–34) (▼), and [Gln$^3$]bPTH(1–34) (◇).

FIG. 7C shows adenylate cyclase (AC) activation produced by bPTH(1–34) (o), [Ala$^6$]bPTH(1–34) (●), [Phe$^6$]bPTH(1–34) (Δ), [Leu$^6$]bPTH(1–34) (▲), [Ser$^6$]bPTH (1–34) (□), and [Glu$^6$]bPTH(1–34) (■).

FIG. 7D shows competitive binding to PTH receptors by bPTH(1–34) (o), [Ala$^3$]bPTH(1–34) (●) [Phe$^3$]bPTH(1–34) (Δ), [Leu$^3$]bPTH(1–34) (▲), and [Tyr$^3$]bPTH(1–34) (□).

FIG. 7E shows competitive binding to PTH receptors by bPTH(1–34) (o), [Glu$^3$]bPTH(1–34) (■), [His$^3$]bPTH (1–34) ▽), [Lys$^3$]bPTH(1–34) (▼), and [Gln$^3$]bPTH(1–34) (◇).

FIG. 7F shows competitive binding to PTH receptors by bPTH(1–34) (o), [Ala$^6$]bPTH(1–34) (●), [Phe$^6$]bPTH (1–34) (Δ), [Leu$^6$]bPTH(1–34) (▲), [Ser$^6$]bPTH(1–34) (□), [Glu$^6$]bPTH(1–34) (■), and [Phe$^9$]humanPTH(1–34) (▽).

FIGS. 8A–B shows inhibition of bPTH(1–34)-stimulated adenylate cyclase activity by the partial agonist [Phe$^6$]bPTH (1–34).

FIG. 8A shows adenylate cyclase (ACY-activation in canine renal plasma membranes produced by bPTH(1–34) (o), [Phe$^6$]bPTH(1–34) (●), and bPTH(1–34) (5nM) in the presence of varying concentrations of [Phe$^6$]bPTH(1–34) (Δ).

FIG. 8B shows adenylate cyclase (AC) activation in UMR 106-H5 cells produced by [Phe$^6$]bPTH(1–34) (o) and by 0.2 nM bPTH(1-34) in the presence of varying concentrations of [Phe$^6$]bPTH(1–34) (●).

DETAILED DESCRIPTION OF THE INVENTION AND PREFERRED EMBODIMENTS

Definitions

Throughout this application the name of an amino acid may be followed by a superscript number. This designation (e.g. Tyr$^{34}$) refers to the amino acid at position 34 of PTH be tyrosine.

"B$^3$" refers to the amino acid B at position 3 of PHT, etc.

"J$^6$" refers to the amino acid J at position 6 of PHT, etc.

"X$^9$" refers to the amino acid X at position 9 of PHT, etc.

The references to specific journal(s) are ususally found in parenthesis (Ref.) at the end of a sentence.

"bPHT" refers to the bovine sequence of PTH having a specific sequence of 1–84 amino acids.

"bPHT(1–34)" refers to a shortened bovine PHT sequence, the sequence of active 1–34 amino acids.

"cPTH" refers to the 1–84 chicken sequence for PTH.

"hPTH" refers to the 1–84 human sequence for PTH.

"hPTH(1–34)" refers to the shortened amino acid sequence for human PTH.

"hPTHrP" refers to the natural human parathyroid hormone related protein of 139–141 amino acids. bPTHrP is derived from bovine cells. hPTHrP is derived from human cells. pPTHrP is derived from porcine cells.

"hPTHrP(1–34)" refers to the active 1–34 amino acids of natural human parathyroid hormone related protein.

"pPTH" refers to the 1–84 porcine anmino acid sequence for PTH.

"pPTH(1–34)" refers to the active 1–34 normal porcine amino acid sequence for pPTH.

As set forth above and for convenience in describing this invention, the conventional abbreviations for the various common amino acids are used as generally accepted in the peptide art as recommended by the IUPAC-IUB Commission on Biochemical Nomenclature, *Biochemistry*, Vol. 11, 1726 (1972) and represent L-amino acids with the exception of the achiral amino acid glycine. All peptide sequences mentioned herein are written according to the generally accepted convention whereby the N-terminal amino acid is on the left and the C-terminal amino acid is on the right. In some polypeptides of the present invention, the terminal —COOH group is converted to the amide group —C(=O) NH$_2$. The polypeptides are identified as the '-amide'. For example, 'Gly-amide' would designate the terminal group, —CH$_2$—C(=O)-NH$_2$.

"Natural amino acids" refer to those well known in the art. They are listed and standard abbreviations are provided in the U.S.P.T.O. publication, *Trademark Official Gazette*, published May 15, 1990, p. 33 at 46. These amino acids and abbreviations are specifically incorporated herein by reference.

The natural amino acids are shown below:

| | | |
|---|---|---|
| A | Ala | alanine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| Q | Gln | glutamine |
| R | Arg | arginine |
| S | Ser | serine |
| T | Thr | threonine |
| V | Val | valine |
| W | Trp | tryptophane |
| Y | Tyr | tyrosine |

Modified (unusual, modified or substituted) amino acids are found in the above cited Trademark Official Gazette at p. 47 and 48. Unusual or modified amino acids include but are not limited to these which are specifically incorporated herein by reference:

| | |
|---|---|
| Aad | 2-Aminoadipic acid |
| bAad | 3-Aminoadipic acid |
| bAla | beta-Alanine, beta-Aminopropionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| bAid | 3-Aminoisobutyric acid |
| Apm | 2-Aminopimelic acid |
| Dbu | 2,4-Diaminobutyric acid |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| aHyl | allo-Hydroxylysine |
| 3Hyp | 3-Hydroxyproline |
| 4Hyp | 4-Hydroxyproline |
| alle | allo-Isoleucine |
| MeGly | N-Methylglycine, sarcosine |
| MeIle | N-Methylisoleucine |
| MeLys | N-Methylvaline |
| Nva | Norvaline |
| Nle | Norleucine |
| Orn | Ornithine |
| Cit | Citrulline |
| | 3, 4 or 5-Fluorohistidine |

Further, unusual or modified "amino acids" include those substituted amino acids which are further substituted on the molecule with another group, such as alkyl or hydroxyl. Typical substituted amino acids include, for example, 4-hydroxy-L-proline, sarcosine ("Sar" also known as N-methylglycine), D-3-(2-naphthylalanine) "D-Nal", $N^5$(aminocarboxyl)-ornithine"Cit", pyro-glutamic acid, ornithine ; pmp (1-B-mercapto-beta,beta-pentamethylene propionic acid; Tyr (Et), tyrosine ethylated at the 4hydroxyl position.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

As used herein, the term "pharmaceutically acceptable salts" refers to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, tannic acid, pamoic acid, alginic acid, polyglutamic acid, naphthalenesulfonic acids, naphthalenedisulfonic acids, polygalacturonic acid; (b) salts with metal (M) cations such as sodium, potassium, zinc, calcium, bismuth, barium, magnesium, aluminum, copper, cobalt, nickel, cadmium, and the like; or with an organic cation formed from N,N'-dibenzylethylenediamine or ethylenediamine; or (c) combinations, of (a) and (b), e.g. a zinc tannate salt and the like.

Description of the Invention

The present invention combines available or derived structure-activity data with predictive and/or experimental determinations regarding the molecular structure of PTH, or PTHrP to identify key amino acid residues in the 1–34 (or larger) amino acid sequences expected to play critical roles in high affinity receptor binding and activation. The analogs containing amino acid substitutions at the 3, 6, or 9 positions or combinations thereof are synthesized and evaluated for the influence of side-chain polarity, charge and size or biological activity. The in vitro bioassay is described for PTH receptor binding and adenylate cyclase activity in canine renal membrane and in rat bone and human bone cells. The results of these in vitro assays are predictive of in vivo biological activity.

Two semi-empirical approaches were used to predict the secondary structural features of mammalian PTH(1–34) and PTHrP(1–34) - statistical (Ref. 22,23) and pattern-based (24,25) (FIG. 2). For PTH(1–34) two helical segments comprising 68% (23/24) to 82% (28/34) of the peptide are predicted, as previously suggested (Ref. 26,27). The putative COOH-region helix contains residues thought to play a direct role in hormone binding to its receptor, whereas the $NH_2$-region helix would include either part of or all of the 1–6 peptide segment required for activation for the receptor (induction of coupling to the stimulatory GTP-binding component of adenylate cyclase, $G_S$. Similarly, two helical segments are predicted for PTHrP(1–34). These would comprise 74% (23/34) to 94% (32/34) of the peptide. Chou-Fasman (Ref. 22) calculations suggest a beta-turn in positions 10–13 of PTH(1–34), and strongly predict a beta-turn in the corresponding region of PTHrP.

Circular dichroism (CD) spectra for bPTH(1–34), [$Tyr^{34}$] bPTH(7–34)amide, and hPTHrP(1–34)amide were obtained in an aqueous buffer in the presence and absence of trifluoroethanol (TFE). In the absence of TFE, bPTH(1–34) yielded a spectrum with a nadir at 208 nm and a broad shoulder in the region of 222 nm (FIG. 3). In the presence of 45% TFE, the nadir at 208 nm deepened, and a second minimum appeared at 222 nm. These results suggest the presence of alpha-helical structure for bPTH(1–34) that is enhanced in the presence of TFE. The ellipticity became positive at wavelengths less than 200 nm, indicating the presence of a small amount of residual beta-structure. Surprisingly, this feature was also enhanced by TFE. The spectra qualities exhibited by hPTHrP(1–34)amide and [Tyr$^{34}$]amide (7–34) were qualitatively similar.

The relationship between alpha-helical content (estimated by deconvolution of CD spectra according to Taylor and Kaiser, Ref. 29) and solvent amphiphilicity for these peptides is presented in FIG. 4. The spectra were consistent with progressively increasing alpha-helical structure with increasing concentrations of TFE. In the presence of 45% TFE, bPTH(1–34) and hPTHrP(1–34) amide were calculated to display, respectively, 25±3 and 24±3 residues contained within alpha-helical domains. These results are predicted by the Chou-Fasman analysis described above. The CD spectrum of the PTH(7–34) analogue was also consistent with the Chou-Fasman analysis. PTH(7–34) contained 7 to 8 fewer alpha-helical residues than either bPTH(1–34) or hPTHrP(1–34)amide, providing direct evidence to suggest that the amino-terminal 1–6 domain of PTH assumes or induces alpha-helical structure in the presence of TFE. This result was confirmed in a second experiment in which [Tyr$^{34}$]bPTH(1–34)amide and [Tyr$^{34}$]bPTH(7–34)amide were calculated to display, respectively 24 and 18 alpha-helical residues in the presence of 30% TFE.

In the absence of TFE, bPTH(1–34), hPTHrP(1–34) amide, and [Tyr$^{34}$]bPTH(7–34)amide are calculated to have 7–10 alpha-helical residues, consistent with a second alpha-helical domain that persists under strictly polar solvent conditions. This latter domain is predicted to lie between residues 17–34 of PTH and PTHrP. These results are similar to previous estimates of less than 12 alpha-helical residues for bPTH(1–34) and hPTH(1–34) (37–39), and 9 alpha-helical resides for bPTH(7–34) (Ref. 37) under aqueous conditions in the absence of amphiphiles. The effect of TFE on the secondary structure of the PTH(7–34) analogue may reflect extension of the putative COOH-region helical domain under conditions of increasing solvent amphiphilicity.

The results indicate that, under appropriate solvent conditions, both bPTH(1–34) and hPTHrP(1–34)amide have extensive secondary structure that is largely alpha- helical. Based on these results, a three-dimensional model of the 1–34 sequences of PTH and PTHrP was constructed by packing the amino-and carboxyl-terminal a-helices together (FIG. 5). A hydrophobic contact surface on the face of each helix was located using the method of Richmond and Richards (Ref., 40). A helical assembly was constructed following the approach of Cohen et al. (Ref. 41). To maintain the connectivity of the chain, the interhelical packing angle was necessarily +20° or –20° (+160° or –160°).

In the context of this model, conserved substitutions at positions 4, 7, and 8 as well as 20, 23, 24, 28, and 31 involve residues buried in the hydrophobic core. Presumably these residues contribute to the stabilization of the folded structure. By contrast, conserved solvent-exposed residues at positions 3, 6, 9, and 12 are likely to participate in critical interactions at the ligand-receptor interface. Twenty-three analogues of bPTH(1–34) monosubstituted at positions 3 or 6 or 9 or disubstituted at positions 3 and 6 were synthesized generally following the procedures for peptide amino acid synthesis and specifically as found in the Experimental section and tested for their inactivity in binding to PTH receptors and activating adenylate cyclase in canine renal plasma membranes and UMR 106-H5 rat osteosarcoma cells (FIGS. 6 and 7, and Tables 1 and 1A). Effects of these substitutions on receptor binding were similar in the kidney and bone systems. At position 3, a diverse array of amino acids including Ala, Leu, Gln, and His were well tolerated (greater than 30% retention of binding potency) whereas Lys, Phe, and Tyr were less well tolerated (2–15% retention of binding potency). [Glu$^3$]bPTH(1–34) retained less than 0.1% receptor binding activity. Substitutions at position 6 resulted in analogues with moderately reduced binding activity, with the exception of [Phe$^6$]bPTH(1–34) which retained only 1% (renal membranes) 4% (osteosarcoma cells) of the activity of bPTH(1–34).

In general, reductions in binding affinity were paralleled by a comparable increase in the concentration of peptide required for stimulation of adenylate cyclase in UMR 106-H5 cells. Exceptions were [Lys$^3$] and [Phe$^3$]bPTH(1–34) which exhibited disproportionately lesser and greater losses in cyclase-stimulating activity, respectively, than expected from, their binding affinities. In contrast, virtually all of the analogues displayed disproportionately low cyclase-stimulating potencies in renal membranes. A similar disparity between renal membrane binding affinity and cyclase-stimulating activity has been noted for PTHrP(1–34) (Ref. 14). Thus, most of the analogues as well as PTHrP are apparently less efficacious than bPTH(1–34) in inducing coupling of the PTH receptor to the activation of adenylate cyclase in canine renal plasma membranes.

Four synthesized analogues exhibited partial agonist activity in the adenylate cyclase assay. Three of these analogues (Phe$^3$, Tyr3, Phe$^6$) involved substitution of hydrophobic residues, whereas the fourth involved a Ser for Gln substitution at position 6. Analogues that exhibited partial agonist behavior did so in both the bone and kidney systems, although to somewhat varying extents. The weak partial agonists were able to inhibit competitively the adenylate cyclase response to the full agonists PTHrP(1–34) and bPTH(1–34) (FIG. 8).

Assays were conducted using UMR-160-H5 cells. These assays were performed as described in Cohen et al. (1991), *J. Biological Chem.*, 266(3), 1997 and in the Experimental section, e.g. Example 11.

In UMR-106-H5 cells, several of the position 3 analogues displayed increased potency for adenylate cyclate activation (Leu$^3$, His$^3$) or increased activity in adenylate cyclase (Tyr$^3$), compounded with renal adenylate cyclase. This result demonstrates that these analogues are relatively bone specific.

Although the analogues tested displayed a wide range of potencies in the receptor binding adenylate cyclase assays, the substitutions produced little effect on secondary structure as evidenced by CD spectroscopy. The calculated alpha-helical content varied only between 29–36% for these peptides, with exception of [Glu$^3$]bPTH(1–34) which displayed 19% alpha-helical content (Table 1). The reduced alpha-helical content of [Glu$^3$]bPTH(1–34) was associated with a dramatic loss of biological activity in both assay systems. For the remainder of the analogues, alterations in biological activity appeared to be independent of major changes in secondary structure.

In Table 1 below, the potency and activity of bPTH(1–34) is designated as 100%, and the peptide analogues are described in percent relative to the bPTH(1–34). The renal membrane assay values listed reflect the effect of the polypeptide analogue with kidney tissue receptors. The UMR-106-H5 assay values reflect the effect of the peptide analogue with rat bone tissue receptors. The Sa05-2 assay values reflect the effect of the peptides for human bone tissue receptors.

Activity is defined as the intrinsic ability to stimulate adenylate cyclase so that a full agonist would have 100% activity. A full antagonist would have 0% activity. A partial agonist would have >0 and <100% activity. An ideal antagonist in either assay would have 100% binding (B) and 0% activity (AC). A superagonist would have greater than 100% (e.g. 200%) binding (B), and 100% activity (AC) in either assay.

A preferred embodiment is a bone specific peptide analogue which would have binding (B) which approaches 0% and 0% activity in soft renal membranes, and approaches or is greater than 100% binding and activity in the UMR 106-H5 assay.

For example, analog [$Tyr^3$ bPHT (1–34)] in Table 1 shows a preferred pattern having low binding and activity in renal tissue and high bind and activity in the UMR-106-H5 assay.

Table 1A describes the potency and activity of hPTH (1–34) designated as 100% and the peptide analogs are described in percent relative to hPTH (1–34) (human).

TABLE 1

BOVINE PTH ASSAY RESULTS

| | RENAL MEMBRANES | | | UMR106-H5 CELLS | | | SAOS2 CELLS | | % HELIX | |
|---|---|---|---|---|---|---|---|---|---|---|
| | Canine | | | Rat Bone | | | Human Bone | | | |
| | Potency | | Activity | Potency | | Activity | Potency | Activity | TFE | |
| | (B) | (AC) | (AC*) | (B) | (AC) | (AC*) | (AC) | (AC) | (0%) | (30%) |
| bPTH (1–34) | 100 | 100 | 100 | 100 | 100 | 100 | | | 35 | 91 |
| $ala^3$ | 79 | 100 | 89 | 38 | 79 | 90 | | | 30 | 100 |
| $leu^3$ | 44 | 3.3 | 85 | 45 | 52 | 92 | | | ND | ND |
| $phe^3$ | 22 | 1 | 39 | 8 | 2 | 80 | | | ND | ND |
| $gln^3$ | 57 | 35 | 100 | 47 | 100 | 100 | | | 31 | 95 |
| $glu^3$ | <0.1 | <0.1 | >30 | 0.2 | <0.1 | >35 | | | 19 | 93 |
| $lys^3$ | 14 | 1.5 | 78 | 3.5 | 14 | 95 | 20 | 100 | 29 | 81 |
| $his^3$ | 55 | 2.5 | 100 | 9 | 75 | 100 | | | 35 | 84 |
| $tyr^3$ | 2 | 1.2 | 28 | 0.9 | 2.5 | 100 | | | 34 | 99 |
| $leu^6$ | 12 | 3.5 | 84 | 6.3 | 7 | 81 | | | 33 | 94 |
| $phe^6$ | 1.3 | 1.4 | 26 | 4.5 | 1.1 | 37 | | | 33 | 99 |
| $ala^6$ | 54 | 4 | 87 | 12 | 22 | 90 | 4 | 80 | 33 | 94 |
| $glu^6$ | 72 | 12 | 100 | 48 | 45 | 100 | | | 36 | 90 |
| $ser^6$ | 15 | 1.3 | 50 | 33 | 4.7 | 35 | | | ND | ND |

Potency and maximal activity for PTH receptor binding (B) and adenylate cyclase activation (AC) for 3, 6 and 9-position modified analogues of bPTH (1–34). Modified analogues are Z = amide.
Refer to Table 1A for definition of B, AC and AC*.
Both are shown as % relative to PTH (1–34) amide, which is assigned a value of 100%. The activity of adenylyl cyclase produced by a maximally effective dose of modified peptide is shown relative to that produced by bPTH (1–34). Also shown in the % of alpha-helical structure calculated from circular dichromism (CD) spectra obtained in the presence and absence of 30% trifluoroethanol (TFE), as described in the EXPERIMENTAL section.

TABLE 1(A)

HUMAN PTH ASSAY RESULTS

| | RENAL MEMBRANES | | | UMR106-H5 CELLS | | | SAOS2 CELLS | | % HELIX | |
|---|---|---|---|---|---|---|---|---|---|---|
| | Canine | | | Rat Bone | | | Human Bone | | | |
| | Potency | | Activity | Potency | | Activity | Potency | Activity | TFE | |
| | (B) | (AC) | (AC*) | (B) | (AC) | (AC*) | (AC) | (AC) | (0%) | (30%) |
| hPTH (1–34) | 100 | 100 | 100 | 100 | 100 | 100 | 100 | 100 | 35 | 91 |
| $gln^9$ | 7 | 2 | 86 | 0.8 | 1.4 | 100 | 100 | 100 | 37 | 86 |
| $ser^9$ | 4 | 0.4 | 57 | 0.4 | 0.6 | 97 | | | 32 | 83 |
| $leu^9$ | 0.2 | 1.8 | 12 | 0.6 | <0.1 | 80 | | | 40 | 85 |
| $glu^9$ | 25 | 4 | 90 | 6 | 11 | 100 | | | 39 | 91 |
| $phe^9$ | 0.7 | 1.5 | 35 | 1.8 | 0.6 | 84 | | | ND | ND |
| $ala^9$ | 0.7 | 1 | 34 | 0.5 | 0.1 | 85 | | | 36 | 83 |
| $lys^3ala^6$ | 0.5 | 2 | 9 | <0.1 | 0.3 | 72 | 10 | 8 | 33 | 46 |
| $his^3ala^6$ | 0.2 | 2 | 9 | <0.1 | 0.4 | 44 | 14 | 6 | 33 | 47 |
| $lys^3glu^6$ | 89 | 10 | 69 | 10 | 10 | 100 | 12 | 100 | 34 | 100 |
| $his^3glu^6$ | 8.9 | 3 | 56 | 0.3 | 0.5 | 100 | 5 | 100 | 30 | 89 |

Potency and maximal activity for PTH receptor binding (B) and adenylate cyclase activation (AC) for 3, 6 and 9-position modified analogues of bPTH (1–34). Modified analogues are Z = amide.
AC is the concentration of modified peptide which produces half maximal enzyme activation (i.e. the mid-point of the curve transition - can be determined from the enclosed figures.
AC* defines the enzyme activity of large doses of modified peptide relative to PTH reference at 100%.

TABLE 1(A)-continued

HUMAN PTH ASSAY RESULTS

| RENAL MEMBRANES | | | UMR106-H5 CELLS | | | SAOS2 CELLS | | | |
|---|---|---|---|---|---|---|---|---|---|
| Canine | | | Rat Bone | | | Human Bone | | % HELIX | |
| Potency | Activity | Potency | | Activity | Potency | Activity | | TFE | |
| (B) | (AC) | (AC*) | (B) | (AC) | (AC*) | (AC) | (AC) | (0%) | (30%) |

Both are shown as % relative to PHT (1–34) amide, which is assigned a value of 100%. The activity of adenyl cyclase produced by a maximally effective dose of modified peptide is shown relative to that produced by hPTH (1–34). Also shown is the % of alpha-helical structure calculated from circular dichromism (CD) spectra obtained in the presence and absence of 30% trifluoroethanol (TFE), as described in the EXPERIMENTAL section. ND is not determined.

The CD data shown are consistent with our prediction on theoretical grounds that PTH(1–34) and PTHrP(1–34) assume alpha-helical structure in both the amino and carboxyl-terminal domains. Therefore, if the peptides are viewed as an ensemble of structures in equilibrium, containing amino-terminal and carboxyl-terminal alpha-helices, increasing concentrations of TFE presumably drive the equilibrium towards increased helical content.

Previous results indicated in a similar increase in the alpha-helical content of hPTH(1–34) in the presence of dimyristoylphosphatidylcholine vesicles (Ref. 42). The nonpolar environment of the specific receptor could also stabilize highly structured forms of PTH and PTHrP.

The proposed model yields a domain structure that includes a hydrophobic core, hydrophilic faces of each helix, and loop between helices. To maximize the burial of hydrophobic surface areas in bPTH and to promote a favorable interaction between the helix dipoles (Ref. 43), a relatively parallel arrangement (interaxial angle - 160°) is expected (see FIG. 5). This packing angle is commonly found in helical proteins (Ref. 44,45). An analogous paired helical structure has been demonstrated for 28residue avian pancreatic polypeptide by X-ray crystallography (Ref. 46).

Barden and Kemp (Ref. 28) recently reported the use of 2D-NMR and CD spectroscopy to characterize the three dimensional structure of PTHrP(1–34)amide and its fragments at pH 4.5. They concluded that the peptide assumes a structure consisting of an N-terminal helix (residues 3–9), two reverse turns (residues 10–13 and 16–19), and C-terminal coil (residues 23–34). Most importantly, these investigators detected NOE cross-peaks between distant residues (Ref. 2–31, 8–28, 11–24) confirming the existence of a compact structure. Helical structure was assigned to the amino-terminal region instead of the carboxyl-terminal region based on an analysis of the $^3J_{\alpha CHNH}$ coupling constants and the CD spectra of PTHrP analogues. The region identified by Barden and Kemp as helical (residues 3–9) has an average $^3J_{\alpha CHNH}$ of 5.4 Hz. Residues 24–30 in the C-terminal region have a similar average $^3J_{\alpha CHNH}$ of 6.1 Hz. However, the CD spectra of PTHrP(1–34), PTHrP(1–25), and PTHrP(7–34) in water were interpreted as showing evidence of an amino-terminal helix only. The CD spectra for bPTH(13–34) and bPTH(19–34) also indicated little if any alpha-helical structure in these peptides under aqueous condition (Ref. 37).

Modifications of PTH(1–34) that destabilize either interhelical interactions or helices themselves should result in reduced biological activity. This appears to be the case for analogues of PTH that have been examined. Disruption of the hydrophobic core either by oxidation of Met[8] to SOMet (in bPTH[1–84]) or by a Leu[28] to Lys[28] substitution in [Gln[22], Lys[28], Leu[30] hPTH(1–34) results in marked (10–50 fold) loss of biological activity (Ref. 49, 50). In contrast, exchanging of or addition of hydrophobic moities as in Met to Nle[8,18], Met to Met-butyl[8,18], Met to Met-butyl[8,18], or NPS-/NAPS-Trp[23] analogues results in little or no loss of bioactivity (Ref. 4, 51–53). Analogues which delete the C-terminal carboxylate (PTH[1–34]amide; [Tyr[34]]PTH(1–]amide; [D(Tyr[34])PTH-(1–34amide) have enhanced biological activity (Ref. 54). If residues 23–34 form an alpha-helix, the relative alignment of peptide dipoles creates an effective negative charge at the C-terminum equal to approximately –½ e (Ref. 43). A C-terminal COO destabilizes the helix through an unfavorable interaction with the dipole. By contrast, a C-terminal amide stabilizes the helix, perhaps increasing biological potency. Similarly, Lys[13] (within the proposed loop region) stabilizes the dipole of the putative N-terminal helix in PTH an dPTHrP. Indeed, deletion of Lys[13] from PTH(1–34) results in a peptide with markedly reduced bioactivity (Ref. 55). In contrast, oxidation of Met[18] is not expected to destabilize interhelical interactions, and [SOMet[18]]bPTH(1–84) retains nearly 50% of the activity of the native hormone (Ref. 49).

In the present invention, a combination of spectro-scopic and predictive methods are used to develop a structural model for PTH (1–34) (F.E. Cohen et al., J. Biol. Chem. 266:1997, 1991). The peptide is envisaged to consist of two amphipathic α-helices separated by a loop. The amino-region a-helix initiates at or near the amino-terminus and extends to approximately residue 10. The second α-helix initiates at about residue 18 and extends to the carboxyl-terminus. The helices are suggested to fold back on one another in an antiparallel fashion, resulting in formation of a hydrophobic core with externally-facing polar residues that are expected to be centrally involved in receptor binding.

Three such polar residues are modified: Ser at position 3; Gln at position 6; and His at position 9. These residues are conserved in all known members of the PTH/PTHrP family (FIG. 1), and may thus interact directly with key receptor determinants. In each case, analogs are synthesized to assess the impact of changes in charge, hydrophobicity, and side-chain volume.

(i) Analogs with altered ability to activate adenylate cyclase once binding occurs.

In the present invention, several peptides displayed a reduced ability to activate adenylate cyclase at maximally effective concentrations. The reduced intrinsic activity of such analogs presumably reflects their failure to convert the receptor to a fully-functional conformation subsequent to binding. For the most part, analogs displaying this behavior have hydrophobic residues substituted for normally polar amino acids at positions 3, 6 and 9. At position 3, substitution of Phe or Tyr for Ser markedly reduced the intrinsic activity of PTH (1–34). As discussed below, this effect is specific for the renal assay, and is not evident in bone cells. The reduced bioactivity is directly related to the volume of the hydrophobic side-chain introduced at position 3, suggesting that this residue is sterically constrained within the receptor pocket. A significant negative correlation was obtained between side-chain volume at position 3 (calculated according to Richards (Ref. 57)) and biological activity in each of the assays. For the various assays, the correlation coefficients ranged from -0.68 (p less than 0.05) to –0.92 (p less than 0.01). Substitution of Phe of Gln at position 6 of PTH (1–34) results in an analog with markedly reduced intrinsic activity in both the renal and bone cell adenylate cyclase assays. Hydrophobic residues are very poorly tolerated at position 9, where substitution of Ala, Leu, or Phe for His produced a loss of intrinsic activity in the renal adenylate cyclase assay. In general, substitution at these positions with polar amino acids produce less of intrinsic biological activity. Exceptions were $Ser^6$ and $Ser^9$ PTH(1–34) each of which displays reduced activity.

Analogs that retain receptor-binding activity, but have reduced intrinsic activity are predicted to act as partial PTH antagonists. This is found to be the case with the two partial agonists tested-[$Phe^3$] and [$Phe^6$]PTH(1–34). The finding that single substitutions convert PTH(1–34) to a partial antagonist is a novel finding and suggests new approaches to the development of potent PTH receptor antagonists.

(ii) Effects of substitutions on secondary structure:

Circular dichroism is used in the art and in this invention to assess the effects of amino acid substitutions on the secondary structure of PTH(1–34). Under aqueous solvent conditions, virtually all of single-substituted analogs display 30–40% α-helical content. The only exception is [$^3$Glu]PTH (1–34) which displays only 19% α-helical content, and shows a marked reduction in biological activity. In 30% trifluorenthanol, solvent conditions similar to those expected in the plasma membrane environment, all of the analogs with single residue substitutions displaying 85% a-helical content. Thus, the aforementioned loss of intrinsic activity are not attributed to a gross change in the secondary structure of the analogs. As described below, combined substitutions at residues 3 and 6 have a profound effect on receptor-active structure and on biological activity.

(iii) Peptide Analogs with altered target cell selectivity.

Certain modifications result in disparate losses of activity in the renal vs. bone cell bioassays. Substitutions of the basic residues Lys or His for $Ser^3$ produces analogs which retained substantial activity in bone cells, but had <3% of the activity of PTH (1–34) in renal membranes. Likewise, [$Glu^6$] and [$Ala^6$]PTH(1–34) retain significantly more activity in rat bone cells than in the renal membrane bioassay. The target cell selectivity of [$Ala^6$]PTH(1–34) appears to be species-dependent since the analog is equipotent in human bone cells and in renal membranes. In contrast, [$Lys^3$]PTH(1–34) has enhanced bioactivity in both bone cell assays, and may thus discriminate between the PTH receptor-adenylate cyclase system in kidney vs bone.

(iv) Peptide analogs with double substitutions.

Substitutions are in positions 3 and 6 which individually do not impact markedly upon activity are introduced in pairs to create a series of analogs substituted in both positions. $Lys^3ala^6$ b-PHT and $his^3ala^6$ b-PHT show low receptor affinity and low cyclase-stimulating activity in bone cells and in membranes from bone cells and kidney. Since single substitutions of alanine or glutamic acid for glutamine at position 6 or of lysine or histamine for serine at position 3 have minimal effects on intrinsic activity, the result suggests that effective activation of the PTH receptor involves an interaction between positions 3 and 6 in the ligand. This interaction evidently preserves helical structure, as the helical content of analogs in which alanine is substituted for glutamine at positions 6 have reduced helical content. In contrast, $lys^3ala^6$ and $his^3ala^6$ are full agonists in all systems. It appears that with a small side-chain in the 6 position, basic residues at position 3 are markedly destabilizing and detrimental to binding, as are other amino acid substitutions which destablize the helix structure.

The amino acid in position 9 is the natural one histidine or is preferably one which will easily accept a positive charge, and thus modify the helical structure, e.g. tyrosine, tryptophan, phenylalanine, diaminobutyric acid, D-Nal, ornithine, citrulline, 3,4 or 5-fluorohistidine and the like.

Selection of Modified Polypeptides Useful as Pharmaceuticals

In an additional aspect of the present inveniton, by use of the assays and their results, it is possible to select those modified peptides which are active for further evaluation to produce useful pharmaceuticals.

This result is accomplished by modifying the peptide (e.g. PTH(1–34) at the 3,6 or 9 position or a combination thereof as described herein, performing an assay using specific soft tissue, membrane or cells, to evaluate receptor binding and activity; and performing an assay using specific bone cells to evaluate solid bone receptor binding and activity. Based on the results of the assay, four categories of useful pharmaceuticals are determined, i.e.

(d) (i) independently selecting those peptide amino acid analogs for further evaluation, having a high binding and high activity in the specific tissues, membranes or cells and a high specific bone cell binding and high activity, as agonists for medical treatment for disease conditions of the tissues, membranes, cells or bone, or alternatively;

(d) (ii) independently selecting those peptide amino acid analogs for further evaluation, having a low binding and high activity as specific agonists for medical treatment in the specific soft tissues, membranes, or cells and a high specific bone cell binding and low activity for disease conditions of the tissues, membranes, or cells, or alternatively;

(d) (iii) independently selecting those peptides for further evaluation as agonists having a low binding and low activity in specific soft tissues, membranes or cells and high specific bone cell binding and high activity for disease condition's of the bone, or alternatively;

(d) (iv) independently selecting high binding and low activity in soft tissues, membranes or cells and in bone cells for use as antagonists in the medical treatment of hormonal disorders and cancers.

Subsequent different standard assays or toxicity determinations are performed on the amino acid analogs pursuant to identifying a useful pharmaceutical.

In one embodiment, in step (d) (i) the high binding and high activity in the specific tissues, membranes or cells and a high specific bone cell binding and high activity are each about 50% or greater than that of the reference peptide.

In one embodiment, in step (d) (ii) the high binding and high activity as agonists for medical treatment in the specific tissues, membranes, or cells is about 50% or greater than that of the reference peptide and the low specific bone cell binding is about 5 to 0% and low activity of bone cell is about 10% or less.

In one embodiment, in step (d) (iii), the low binding is less than 10% and the low activity is about 5 to 0% in specific tissue, and high specific bone cell binding and the high activity is about 50% or greater, for disease conditions of the bone.

In one embodiment, in step (d) (iv) the high binding is greater than 50% and the low activity is essential 5 to 0% in soft tissues, membranes or cells or in bone, for use as pharmaceutical antagonists in the medical treatment of hormonal disorders and cancers.

Preferably, the soft tissue etc. are derived from human or bovine kidey.

Thus, based on the present selection process (glu$^6$ or ala$^3$)bPTH(1–34) amide is useful as an agonist for soft tissue or for bone, (d),(i).

Similarly, phe$^6$bPTH(1–34) amide is selected as being useful as a specific agonist for disease-conditions in soft tissue, etc., (d), (ii).

Similarly, phe$^3$ bPTH(1–34) amide is selected as being useful as a specific agonist for disease conditions in bone (d)(iii).

Also, ser$^6$ bPTH(1–34) amide is selected as an antagonist for disease conditions in soft tissue and bone (d), (iv).

In summary, the present invention describes a model for the structures of PTH(1–34) and PTHrP(1–34) in which their biologically active conformations at the receptor consist of N- and C-terminal amphiphilic helices connected by a loop of approximately 12 residues. Interhelical interactions result in a hydrophobic core with externally-facing hydrophilic residues that presumably include determinants of receptor binding and activation. The synthesis of analogues substituted in two such externally-facing positions permits the demonstration that amino acid positions 3, 6 or 9 contribute important determinants of receptor binding and activation. Further delineation of the structural constraints at these positions will facilitate the rational design of potent PTH antagonists.

Specific embodiments of the present invention include the following wherein serine is at position 1 and the amino acid at position 3 is different. Group A' is independently selected from the remaining peptides of the 1-34 active unit of hPTH, PPTH, bPTH, or their Z=COOH or COO-+M or -(C=O)NH$_2$ terminated derivatives; or the remaining 4–84 sequence of hPTH or bPTH or hPTHrP:

H$_2$-N-Ser-Val-Lys-A';
H$_2$N-Ser-Val-Phe-A';
H$_2$N-Ser-Val-Leu-A';
H$_2$N-Ser-Val-Ala-A';
H$_2$N-Ser-Val-Thr-A';
H$_2$N-Ser-Val-Cys-A';
H$_2$N-Ser-Val-Tyr-A';
H$_2$N-Ser-Val-Asp-A';
H$_2$N-Ser-Val-Glu-A';
H$_2$N-Ser-Val-Asn-A';
H$_2$N-Ser-Val-Gln-A';
H$_2$N-Ser-Val-Lys-A';
H$_2$N-Ser-Val-Arg-A';
H$_2$N-Ser-Val-His-A';
H$_2$N-Ser-Val-Val-A';
H$_2$N-Ser-Val-Ile-A';
H$_2$N-Ser-Val-Trp-A';
H$_2$N-Ser-Val-Met-A';
H$_2$N-Ser-Val-Pro-A';
H$_2$N-Ser-Val-Nle-A';
H$_2$N-Ser-Val-D-Nal-A'; or
H$_2$N-Ser-Val-Orn-A'.

In all of the mofified peptide amino acid sequences described herein, Z=amide is preferred. The Z=amide analog is more preferred for the peptide sequences described in any of the claims below.

In the analogues of the following list, the amino acid at position 1 is alanine, and the amino acid at position 3 is varied:

H$_2$N-Ala-Val-Ala-A';
H$_2$N-Ala-Val-Thr-A';
H$_2$N-Ala-Val-Cys-A';
H$_2$N-Ala-Val-Tyr-A';
H$_2$N-Ala-Val-Asp-A';
H$_2$N-Ala-Val-Glu-A';
H$_2$N-Ala-Val-Asn-A';
H$_2$N-Ala-Val-Gln-A';
H$_2$N-Ala-Val-Lys-A';
H$_2$N-Ala-Val-Arg-A';
H$_2$N-Ala-Val-His-A';
H$_2$N-Ala-Val-Val-A';
H$_2$N-Ala-Val-Leu-A';
H$_2$N-Ala-Val-Ile-A';
H$_2$N-Ala-Val-Pro-A';
H$_2$N-Ala-Val-Phe-A';
H$_2$N-Ala-Val-Trp-A';
H$_2$N-Ala-Val-Met-A';
H$_2$N-Ala-Val-Nle-A';
H$_2$N-Ala-Val-D-Nal-A'; or
H$_2$N-Ala-Val-Orn-A'".

More preferred are these analogues are where A' is the 4–34 amino acid sequence of hPTH, especially those having derivatives terminating in Z=-(C=O)-NH$_2$.

Additional specific embodiments of the present invention include the following analogs wherein the amino acid at positions 1 and 3 are both serine, the amino acid at position 6 is replaced by Group J, and Group B'is independently selected from the remainder of the remaining peptides of the 7–34 active unit of hPTH, or bPTH, or pPTH, or their Z=COOH or COO-+M or amide derivative, or the 7–84 sequence of hPTH or bPTH or pPTH or hPTHrP:

H$_2$N-Ser-Val-Ser-Glu-Ile-Ala-B';
H$_2$N-Ser-Val-Ser-Glu-Ile-Thr-B';
H$_2$N-Ser-Val-Ser-Glu-Ile-Cys-B';
H$_2$N-Ser-Val-Ser-Glu-Ile-Tyr-B';
H$_2$N-Ser-Val-Ser-Glu-Ile-Asp-B';
H$_2$N-Ser-Val-Ser-Glu-Ile-Glu-B';
H$_2$N-Ser-Val-Ser-Glu-Ile-Asn-B';
H$_2$N-Ser-Val-Ser-Glu-Ile-Ser-B';
H$_2$N-Ser-Val-Ser-Glu-Ile-Lys-B';
H$_2$N-Ser-Val-Ser-Glu-Ile-Arg-B';
H$_2$N-Ser-Val-Ser-Glu-Ile-His-B';
H$_2$N-Ser-Val-Ser-Glu-Ile-Val-B';
H$_2$N-Ser-Val-Ser-Glu-Ile-Leu-B';
H$_2$N-Ser-Val-Ser-Glu-Ile-Ile-B';
H$_2$N-Ser-Val-Ser-Glu-Ile-Pro-B';
H$_2$N-Ser-Val-Ser-Glu-Ile-Phe-B';
H$_2$N-Ser-Val-Ser-Glu-Ile-Trp-B';
H$_2$N-Ser-Val-Ser-Glu-Ile-Met-B';

H₂N-Ser-Val-Ser-Glu-Ile-Gly-B';

H₂N-Ser-Val-Ser-Glu-Ile-Nle-B';

H₂N-Ser-Val-Ser-Glu-Ile-D-Nal-B'; or

H₂N-Ser-Val-Ser-Glu-Ile-Orn-B'.

Additional specific embodiments of the present invention include the following wherein Group B'is selected from the remainder of the remaining peptides of the 7–34 active unit of hPTH or bPTH or their Z=COOH or COO-+M or amide derivative, or remaining 7–84 sequence of hPTH, bPTH, pPTH, or hPTHrP. In the list of analogs which follow the amino acid at position 1 is alanine and position 3 is serine, and position 6 is a variety of amino acids.

H₂N-Ala-Val-Ser-Glu-Ile-Ala-B';

H₂N-Ala-Val-Ser-Glu-Ile-Thr-B';

H₂N-Ala-Val-Ser-Glu-Ile-Cys-B';

H₂N-Ala-Val-Ser-Glu-Ile-Tyr-B';

H₂N-Ala-Val-Ser-Glu-Ile-Asp-B';

H₂N-Ala-Val-Ser-Glu-Ile-Glu-B';

H₂N-Ala-Val-Ser-Glu-Ile-Asn-B';

H₂N-Ala-Val-Ser-Glu-Ile-Ser-B';

H₂N-Ala-Val-Ser-Glu-Ile-Lys-B';

H₂N-Ala-Val-Ser-Glu-Ile-Arg-B';

H₂N-Ala-Val-Ser-Glu-Ile-His-B';

H₂N-Ala-Val-Ser-Glu-Ile-Val-B';

H₂N-Ala-Val-Ser-Glu-Ile-Leu-B';

H₂N-Ala-Val-Ser-Glu-Ile-Ile-B';

H₂N-Ala-Val-Ser-Glu-Ile-Pro-B';

H₂N-Ala-Val-Ser-Glu-Ile-Phe-B';

H₂N-Ala-Val-Ser-Glu-Ile-Trp-B';

H₂N-Ala-Val-Ser-Glu-Ile-Met-B';

H₂N-Ala-Val-Ser-Glu-Ile-Gly-B';

H₂N-Ala-Val-Ser-Glu-Ile-Nle-B'; or

H₂N-Ala-Val-Ser-Glu-Ile-D-Nal-B';

H₂N-Ala-Val-Ser-Glu-Ile-Orn-B'.

Additional specific embodiments of the present invention include the following wherein Group B'is selected from the remainder of the remaining peptides of the 7–34 active unit of hPTH or bPTH or PPTH, or their Z=COOH or COO-+M or amide derivative, or remaining 7–84 sequence of hPTH, bPTH, PPTH or hPTHrP:

H₂N-Ser-Val-Phe-Glu-Ile-Phe-B';

H₂N-Ser-Val-Phe-Glu-Ile-Ser-B';

H₂N-Ser-Val-Tyr-Glu-Ile-Phe-B';

H₂N-Ser-Val-Tyr-Glu-Ile-Ser-B';

hd 2N-Ser-Val-Phe-Glu-Ile-Ala-B';

H₂N-Ser-Val-Lys-Glu-Ile-Ala-B';

H₂N-Ser-Val-His-Glu-Ile-Ala-B';

H₂N-Ser-Val-Leu-Glu-Ile-Ala-B';

H₂N-Ser-Val-His-Glu-Ile-Glu-B';

H₂N-Ser-Val-Leu-Glu-Ile-Glu-B';

H₂N-Ser-Val-Lys-Glu-Ile-Glu-B';

H₂N-Ser-Val-Phe-Glu-Ile-Glu-B';

H₂N-Ser-Val-Nle-Glu-Ile-Glu-B';

H₂N-Ser-Val-D-Nal-Glu-Ile-Glu-B';

H₂N-Ser-Val-Orn-Glu-Ile-Glu-B';

H₂N-Ala-Val-Phe-Glu-Ile-Phe-B';

H₂N-Ala-Val-Phe-Glu-Ile-Ser-B';

H₂N-Ala-Val-Tyr-Glu-Ile-Phe-B';

H₂N-Ala-Val-Tyr-Glu-Ile-Ser-B';

H₂N-Ala-Val-Phe-Glu-Ile-Ala-B';

H₂N-Ala-Val-Lys-Glu-Ile-Ala-B';

H₂N-Ala-Val-His-Glu-Ile-Ala-B';

H₂N-Ala-Val-Leu-Glu-Ile-Ala-B';

H₂N-Ala-Val-His-Glu-Ile-Glu-B';

H₂N-Ala-Val-Leu-Glu-Ile-Glu-B'; or

H₂N-Ala-Val-Lys-Glu-Ile-Glu-B'.

More preferred are those active 1–34 amino acid sequences of hPTH, especially those amino acid sequences terminating in Z=COOH or COO-+M or (C=O)NH₂.

In the analogues of the following list, the amino acid at position 1 is serine, and the amino acid at position 3 is varied and the amino acid at position 6 is varied and position 9 is His. Group D'is selected from the remainder of the remaining amino acids of the 10–34 active unit of hPTH, or bPTH or pPTH, or the Z=COOH or COO—+M or (C=O)NH₂ derivative or the remaining 10–84 amino acids of hPTH, bPTH, pPTH, or hPTHrP:

H₂N-Ser-Val-Phe-Glu-Ile-Gln-Leu-Met-His-D';

H₂N-Ser-Val-Phe-Glu-Ile-Ser-Leu-Met-His-D';

H₂N-Ser-Val-Ser-Glu-Ile-Phe-Leu-Met-His-D';

H₂N-Ser-Val-Ser-Glu-Ile-Ser-Leu-Met-His-D';

H₂N-Ser-Val-Tyr-Glu-Ile-Gln-Leu-Met-His-D';

H₂N-Ser-Val-Tyr-Glu-Ile-Ser-Leu-Met-His-D';

H₂N-Ser-Val-Phe-Glu-Ile-Phe-Leu-Met-His-D';

H₂N-Ser-Val-Tyr-Glu-Ile-Phe-Leu-Met-His-D'; or

H₂N-Ser-Val-Phe-Glu-Ile-Nle-Leu-Met-Phe-D'.

In the analogs of the following list the amino acid at position 1 is serine, B³ is serine and J is glutamine and only the amino acid X at position 9 is different. D' is defined above:

H₂N-Ser-Val-Ser-Glu-Ile-Gln-Leu-Met-Ala-D';

H₂N-Ser-Val-Ser-Glu-Ile-Gln-Leu-Met-Ser-D';

H₂N-Ser-Val-Ser-Glu-Ile-Gln-Leu-Met-Leu-D';

H₂N-Ser-Val-Ser-Glu-Ile-Gln-Leu-Met-Phe-D';

H₂N-Ser-Val-Ser-Glu-Ile-Gln-Leu-Met-Tyr-D';

H₂N-Ser-Val-Ser-Glu-Ile-Gln-Leu-Met-Glu-D';

H₂N-Ser-Val-Ser-Glu-Ile-Gln-Leu-Met-Lys-D';

H₂N-Ser-Val-Ser-Glu-Ile-Gln-Leu-Met-Gln-D'; or H₂N-Ser-Val-Ser-Glu-Ile-Gln-Leu-Met-Nle-D.

In the amino acid analogues of the following list, the amino acid at position 1 is alanine, the amino acid at position 3 is serine, amino acid J at position 6 is glutamine, and the only amino acid X at position 9 is different. D'is defined above:

H₂N-Ala-Val-Ser-Glu-Ile-Gln-Phe-Met-Ala-D';

H₂N-Ala-Val-Ser-Glu-Ile-Gln-Phe-Met-Ser-D';

H₂N-Ala-Val-Ser-Glu-Ile-Gln-Phe-Met-Leu-D';

H₂N-Ala-Val-Ser-Glu-Ile-Gln-Phe-Met-Phe-D';

H₂N-Ala-Val-Ser-Glu-Ile-Gln-Phe-Met-Tyr-D';

H₂N-Ala-Val-Ser-Glu-Ile-Gln-Phe-Met-Glu-D';

H₂N-Ala-Val-Ser-Glu-Ile-Gln-Phe-Met-Lys-D';

H₂N-Ala-Val-Ser-Glu-Ile-Gln-Phe-Met-Gln-D';

H₂N-Ala-Val-Ser-Glu-Ile-Gln-Phe-Met-Nle-D'; or

H₂N-Ala-Val-Ser-Glu-Ile-Gln-Phe-Met-D-Nal-D.

In the analogues of the following list, the amino acid at position 1 is alanine, and X is phe and only the amino acids (B,J) at positions 3 and 6 are different. D'is defined above:

H₂N-Ala-Val-Phe-Glu-Ile-Gln-Phe-Met-His-D';

H₂N-Ala-Val-Phe-Glu-Ile-Ser-Phe-Met-His-D';

H₂N-Ala-Val-Ser-Glu-Ile-Phe-Phe-Met-His-D';
H₂N-Ala-Val-Ser-Glu-Ile-Ser-Phe-Met-His-D';
H₂N-Ala-Val-Tyr-Glu-Ile-Gln-Phe-Met-His-D';
H₂N-Ala-Val-Tyr-Glu-Ile-Ser-Phe-Met-His-D';
H₂N-Ala-Val-Phe-Glu-Ile-Phe-Phe-Met-His-D';
H₂N-Ala-Val-Tyr-Glu-Ile-Phe-Phe-Met-His-D';
H₂N-Ala-Val-Nle-Glu-Ile-Phe-Phe-Met-His-D'; or
H2N-Ala-Val-D-Nal-Glu-Ile-Phe-Phe-Met-Phe-D'.

DETAILED DESCRIPTION OF THE SYNTHESIS OF POLYPEPTIDES

The polypeptides of the present invention are prepared by the synthesis techniques known in this art. The teachings of the U.S. Pat. Nos. 4,318,905 and 3,531,258 are specifically incorporated herein by reference. A key feature of the present invention is the preparation of biologically active synthetic polypeptides wherein at least the 3 amino acid B, or the 6 amino acid, or the 9 amino acid X, or combinations thereof are replaced a with natural, unusual or synthetic amino acid analogue.

The polypeptides of the present invention may be synthesized by any techniques that are known to those skilled in the peptide art. An excellent summary of the many techniques so available may be found in J. M. Stewart and J. D. Young, "Solid Phase Peptide Synthesis", 2nd ed., Pierre Chem. Co., Rockford, Ill., (1969) and J. Meinenhofer, "Hormonal Proteins and Peptides," Vol. 2, p. 46, Academic Press (New York), 1973 for solid phase peptide synthesis and E. Schroder and K. Lubke, "The Peptides", Vol. 1, Academic Press (New York), 1965 for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compound of the present invention involves solid phase peptide synthesis.

In this particularly preferred method the alpha-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Cbz), biphenylisopropyloxycarbonyl, t-amyloxycarbonyl, isobornyloxycarbonyl, alpha,alpha-dimethyl-3.5-dimethoxybenzyloxycarbonyl, o-nitrophenylsulfenyl, 2-cyano-t-butyloxycarbonyl, 9-fluoroenylmethyloxycarbonyl and the like, especially t-butyloxcarbonyl (Boc).

Particularly preferred side chain protecting groups are, for arginine:nitro, p-toluenesulfonyl, 4methoxybenzenesufonyl, Cbz, Boc and adamantyloxycarbonyl; for tyrosine:benzyl, o-bromobenzyloxycarbonyl, 2,6dichlorobenzyl, isopropyl, cyclohexyl, cyclopentyl and acetyl; for serine:benzyl and tetrahydropyranyl; for histidine; benzyl, p-toluenesulfonyl and 2,4-dinitrophenyl.

The C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer, and the like, especially chloromethyl-polystyrene-1% divinyl-benzene polymer. For the special case where the C-terminus of the compound will be glycinamide, a particularly useful support is the benzhydrylaminopolystyrene-divinylbenzene polymer described by P. Rivaille, et al. *Helv. Chim. Acta.* 54 2772 (1971). The attachment to the chloromethyl polystyrene-divinylbenzene, type of resin is made by means of the reaction of the $N^{aLPha}$-protected amino acid, especially the Boc-amino acid, as its cesium, tetramethylammonium, triethylammonium, 4,5-diazabicyclo[5.4.0]undec-5-ene, or similar salt in ethanol, acetonitrile, N,N-dimethylformamide (DMF), and the like, especially the cesium salt in DMF, with the chloromethyl resin at an elevated temperature, for example between 400 and 60° C., preferably about 50°C., for from about 12 to 48 hours, preferably about 24 hours. The $N^{LaLPa}$-Boc-amino acid is attached to the benzhydrylamine resin by means of an N,N'dicyclohexylcarbodiimide (DCC)/1-hydroxybenzatriazole (HBT) mediated coupling for from about 2 to about 24 hours, preferably about 12 hours at a temperature of between about 10° and 50° C., preferably 25° C., in a solvent such as dichloromethane or DMF, preferably dichlormethane. The coupling of successive protected amino acids can be carried out in an automatic polypeptide synthesizer as is well known in the art. The removal of the $N^8$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in approximately 2.5 molar excess and the coupling may be carried out in dichloromethane dichloromethane/DMF mixtures. DMF and the like, especially in methylene chloride at about ambient temperature. The coupling agent is normally DCC in dichloromethane but may be N,N'-di-iso-propylcarbodiimide or other carbodiimide either alone or in the presence of HBT, N-hydroxysuccinimide, other N-hydroximides or oximes. Alternately protected amino acid active esters (e.g., p-nitrophenyl, pentafluorophenyl and the like) or symmetrical anhydrides may be used.

At the end of the solid phase synthesis, the fully protected polypeptide is removed from the resin support is of benzyl ester type, cleavage is by means of aminolysis with alky-lamine or fluoroalkylamine for peptides with a proline C-terminus, or by aminolysis with, for example, ammonia/methanol or ammonia/ethanol for peptides with a glycine C-terminus at a temperature between 10° and 50° C., preferably about 25° C., for between about 12 and 24 hours preferably about 18 hours. Alternatively, the peptide may be removed from the resin by transesterification, e.g., with methanol, followed by aminolysis. The protected peptide may be purified at this point by HPLC or by silica gel chromatography.

The specific peptide synthesis and purfication steps are described below in the Examples and are summarized in Tables 2,3 and 4.

Utility

The modified peptide analogs of the present invention, i.e. those PTH, etc. analogs having modified amino acids at the 3,6 or 9 positions, or combinations of substitution at the 3,6 and 9 positions, are useful as agonists or as antagonists for treatment of medical conditions or diseases involving parathyroid hormone, particularly in a human being. The diseases etc. are described herein.

Administration

The exact doses and regimen for administration of these compounds and compositions will necessarily be dependent upon the needs of the individual subject being treated, the type of treatment, the degree of affliction or need and, of course, the judgment of the medical practitioner. In general, parenteral administration requires lower dosage than other methods of administration which are more dependent upon absorption. However, certain agents, such as dimethyl sulfoxide, appear to enhance the movement of polypeptide compounds through the skin.

Compositions

A further aspect of the present invention relates to pharmaceutical compositions containing as an active ingredient, a compound of the present invention the compositions comprise a compound in admixture with a pharmaceutically acceptable non-toxic carrier (excipient). As mentioned above, such compositions may be prepared for use for parenteral (subcutaneous, intramuscular or intravenous) administration particularly in the form of liquid solutions or suspensions; for use in vaginal or rectal administration particularly in semisolid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well-known in the pharmaceutical art, for example as described in Remington's *Pharmaceutical Sciences,* Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for vaginal or rectal administration, e.g. suppositories, may contain as excipients, for example, polyalkyleneglycols, vaseline, cocoa butter, and the like. Formulations for inhalation administration may be solid and contain as excipients, for example, lactose or may be aqueous or oily solutions for administration in the form of nasal drops. For buccal administration excipients include sugars, calcium stearate, magnesium stearate, pregelinatined starch, and the like.

It is often desirable to deliver the compounds of the present invention to the subject over prolonged periods of time, for example, for periods of one week to one year from a single administration. Various slow release, depot or implant dosage forms may be utilized. For example, a dosage form a may contain a pharmaceutically acceptable non-toxic salt of the compounds which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above may also be formulated in cholesterol matrix silastic pellets, particularly for use in animals. Additional slow release, depot or implant formulations, e.g. liposomes, are well known in the literature. See, for example, "Sustained and Controlled Release Drug Delivery Systems", J. R. Robinson ed., Marcel Dekker, Inc., N.Y., 1978.

The following Examples are presented for the purpose of description and illustration only. They are not to be construed as limiting in any way.

MATERIALS

Synthetic bovine PTH(1–34) was obtained from Bachem, Inc., Torrance, Calif. Synthetic human PTHrP(1–34)amide was obtained from Merck Sharp and Dohme, West Point, Pa. Synthetic bovine [$Tyr^{34}$]PTH(7 –34)amide and [$Tyr^{34}$]PTH (7–34)amide were obtained from Peninsula Laboratories, Inc., Belmont, Calif. The purity of these peptides exceeded 95% by HPLC. Appropriate peptide composition was verified by quantitative amino-acid analysis.

CD SPECTROSCOPY

Far ultraviolet circular dichroism (CD) spectra were obtained in phosphate buffer (ph 7.0) at 25±1° C. in a 1.0 mm cell on an Instruments SA Jobin Yvon circular dichrograph calibrated with (+) 10-camphorsulfonic acid and epiandosterone. Peptides were analyzed at concentrations ranging from 0.1–0.3 mg/ml. The mean molar ellipticity per residue at 222 nm ([⊖]222 nm-, deg $cm^2$/dmol) was used to derive estimates of alpha-helicity according to the method of Taylor and Kaiser (ref. 29).

PEPTIDE SYNTHESIS AND PURIFICATION

Peptide synthesis was carried out using an Applied Biosystems Model 430A Peptide Synthesizer, Foster City, Calif. A t-Boc-Phe—$OCH_2$-Pam resin was used as the solid support, and the following t-Boc (tert-butyloxycarbonyl) amino acid derivatives were employed: Arg(Tos), Asp (OBzl), Glu(OBzl), His(DNP), His(Z), Lys(Cl-Z), Ser(Bzl), Thr(Bzl), Trp(CHO), and Tyr(Br-Z). A standard program (pre-formed symmetric anhydrides and pre-formed HOBt esters) with inclusion of capping cycles were used. The general synthesis of the peptides is found, for example, in U.S. Patent No. 4,318,905 which is specifically incorporated herein by reference in its entirety.

The following Examples are only provided to be descriptive and explanatory. They are not to be construed to be limiting in any way.

Variations in synthesis are described herein below and summarized in Tables 2,3 and 4.

EXAMPLE 1

Peptide Preparation

Standard t-Boc cycles exist for the activation, solvent exchange, and coupling processes; called ACT, CONC, and RV cycles, respectively. The set of vessel cycl assignments in a standard t-Boc static run file is designated for each amino acidon the basis of testing and synthesis optimization performed at Applied biosystems.

Descriptions of the cycles assigned in the static run are described later under "Activator Cycles (ACT)", "Concentrator Cycles (CONC)I", and Reaction Vessel Cycles (RV)". Other vessel cycles for synthesis are also included.

All amino acids with the exception of Arg, Asn, and Gln are activated to symmetric anhydride using 1 mmol of 0.5 M DCC in DCM. The by-product of this reaction, DCU, begins to precipitate almost immediately. The total activation time allotted for each cycle is eight minutes. Four of these eight minutes are for purging excess DCM from the solution, allowing approximately 2 mL of DCM to be removed. The purging also cools the solution which aids the DCU precipitation.

When the activation is complete the amino acid solution is transferred from the ACT to the CONC. A complete wash of the transfer line proceeds and follows each transfer between vessels. This procedure ensures that the line is clean both before and after the transfer, and eliminates the possibility of amino acid carry-over between cycles.

Transfer times of the activated amino acid solution to the CONC are longer for aboc 4 cycle than for the aboc 1, aboc 2 or aboc 3; again because of the larger solution volume handled in the aboc 4 ACT cycle. Two DCM rinses of the ACT are transferred into the CONC in all single couple cycles. The time listed in Table 2 includes the initial activation time and purging time.

At the end of the activation and purging, the amino acid solution is ready for transfer to the CONC. A complete wash of the transfer line precedes and follows each transfer between vessels. This procedure ensures that the line is clean both before and after the transfer to eliminate the possibility of carry-over between cycles. The activated amino acid solution is transferred to the CONC along with one subsequent DMF rinse of the ACT.

The HOBt-ester activation cycles produce twice as much DCU as the symmetric anhydride cycles; therefore, a more extensive washing process is required after the transfer. This washing consists of two 50:50 DCM:MeOH washes followed by three DCM washes. The first DCM:MeOH wash almost fills the vessel; any DCU carried to the top of the vessel during the purging will be dissolved in this wash. The second DCM:MeOH solution ensures the removal of any DCU adhering to the frit. The residual MeOH is rinsed away with three subsequent DCM washes.

TABLE 2

SINGLE COUPLE ACTIVATOR CYCLES

| CYCLE NAME | DESIGNATED AMINO ACID | DISSOLVING SOLVENT (about) | DISSOLVING TIME (MIN.) (about) | TRANSFER TIMES* (Sec) |
|---|---|---|---|---|
| aboc 1 | Ala, Asp(OBzl), Cys(4-Me-Bzl), Cys(p-OMeBzl) Glu(OBzl), Gly, Ile, Met, Phe, Ser(Bzl), Thr(Bzl), Tyr(Br—Z), Val | 3 mL DCM | 2 | 1 = 30<br>2 = 23 |
| aboc 2 | Lys(Cl—Z), Pro His(Tos)-dry | 3 mL DCM | 8 | 1 = 35<br>2 = 23 |
| aboc 3 | Leu, Met(O), Trp, Trp(CHO) | 0.3 mL DMF 2.5 mL. DCM (2 separate DCM deliveries) | 7 | 1 = 30<br>2 = 23 |
| aboc 4** | His (Tos) | Pre-dissolved in 7 mL DCM | 0 | 1 = 40 |

*1 = Transfer from amino acid cartridge to the Activator
2 = Transfer from the Activator to the Concentrator
**aboc 4 is used to His(Tos)DCHA after the completion of the ion exchange procedure

TABLE 3

DOUBLE COUPLING ACTIVATOR CYCLES

| CYCLE NAME | AMINO ACID | DISSOLVING SOLVENT | DISSOLVING TIME | ACTIVATED DERIVATIVE | ACTIVATION TIME |
|---|---|---|---|---|---|
| aboc 1d | Asn, Gln | 4.0 mL HOBt 0.3 mL DCM | 6.5 min | HOBt Ester | 33 min |
| aboc 2d | Arg(Tos) | 4.0 mL HOBt 1.5 mL DCM | 8 min | HOBt Ester | 33 min |
| aboc 3d | Arg(MTS) | 4.0 mL HOBt 1.5 mL DCM | 8 min | HOBt Ester | 48 min |
| aboc 4d | His(Tos) | Predissolved in 7 mL DCM | 0 min | Symmetric Anhydride | 8 min |

**aboc 4d is used to double couple His(Tos)DCHA after the completion of the ion exchange procedure

TABLE 4

| CYCLE NAME | AMINO ACIDS | TOTAL TIME | PURGE INTERVALS | DMF ADDITION (about) | HEATER SETTING/ USAGE |
|---|---|---|---|---|---|
| Single couple: | | | | | |
| cboc 1 | Ala | 13 min | 4 min<br>5 min<br>4 min | 2 mL<br>2 mL | 15° C./turned on after 1st DMF delivery |
| cboc 2 | Asp(OBzl), Cys(4me-Bzl), Glu(OBzl), Ile, Met, Met(O), Phe, Pro, Ser(Bzl), Thr(Bzl), Trp**, Val | 16 min | 10 min<br>6 min | 2 mL<br>2 mL | 15° C./turned on after 1st DMF Cys (p-MeBzl), delivery |
| cboc 3 | Leu Trp(CHO)** | 14 min | 10 min<br>4 min* | 1 mL<br>3 mL | 5° C./turned on after 1st DMF delivery |
| cboc 4 | Lys(Cl—Z) Tr(Br—Z) | 6 min | 5 min*<br>1 min* | 1 mL<br>3 mL | 15° C./turned on immediately |
| cboc 5 | Gly, His(Tos) | 6.5 min<br>0.5 min | 6 min<br>— | 1 mL | 10° C./turned on immediately |
| Double couple: | | | | | |
| cboc 1d | Arg(Tos) Arg(MTS) ASN, Gln | 0 min | 0 min | — | 10° C./heater not used |
| cboc 2d | His(Tos) | 6.5 min | 6 min<br>0.5 min | 1 mL<br>— | 10° C./heater not used |
| Recouple: | | | | | |
| C recpl | All single coupled amino acids | 0 min | 0 min | — | 10° C./heater not used |

*Multiple short purges
**Heater temperature setting is 25° C.

The c recouple cycle is present on the standard, but is not assigned in the standard t-Boc run. This cycle is simply a transfer cycle designed to recouple any amino acid using DCM as the coupling solvent. This cycle does not include purging or heater use because the initial solvent DCM, is not exchanged for a different coupling solvent, DMF. The amino acid solution is transferred to the RV along with two additional DCM rinses of CONC.

The c recpl cycle should be used in conjunction with the normal single couple ACT cycle, and either recpl2 or recpl2r, the DCM RV recoupled cycles.

EXAMPLE 2

Reaction Vessel (RV) Cycles

There are two types of RV cycles; those that take resin sample and those that do not. Resin-sampling cycles rinse the sampling line several times from the lower RV valve block up through the bulkhead fitting and into the RV. This rinse prevents accumulation of resin, TFA, or coupling solution in the line.

Resin-sampling cycles have an "r" at the end of the cycle name (i.e., rboc lr). If the cycle has "ur" at the end (i.e., rboc lrr), then two resin samples are taken after the coupling. The "rr" cycles are included on this disk for installation purposes. The RV cycles with the same number designation, such as rboc 1 and rboc 1, are the same cycles, except that the resin sampler is used in the latter cycles.

EXAMPLE 3
Single Couple Cycles-rboc 1. 2, 1r, 2r, 1rr, 2rr
All the single couple RV cycles conform to the following pattern:
1. 33% TFA in DCM for 80 seconds
2. 50% TFA in DCM for 18.5 minutes
3. Three DCM washes
4. 10% DIEA in DMF for 1 minute
5. 10% DIEA in DMF for 1 minute
6. Five DMF washes
7. Coupling period
8. Five DCM washes There are two versions of single coupling RV cycles;

these vary only in the length of the coupling period, the time when the deprotected resin-bound peptide is in solution with the activated amino acid. This period begins after "Ready to Receive" step and ends when the amino acid solution is drained from RV. The rboc 1 cycle and its associated resin-sampling cycles, rboc 1r.

Five extensive DMF washes ensure the complete removal of DIEA from the resin RV, and associates lines prior to coupling. The RV is now ready to receive the coupling solution from the CONC, so that the coupling period may ensue.

There are five DCM washes immediately following the coupling period to wash away uncoupled amino acid and DMF. As a secondary function, these washes provide a sampling solution. If one resin sample is taken, at last wash provides the medium for the sample. The double resin-sampling cycles (i.e., "rr" cycles) use the third and fifth wash to collect the two resin samples.

EXAMPLE 4

Double Couple Cycles-rboc, 1d, 2d, 1dr, 1dr

All the double couple RV cycles use the following pattern:
1. 33% TFA in DCM for 80 seconds
2. 50% TFA in DCM for 18.5 minutes
3. Three DCM washes
4. 10% DIEA in DMF for 1 minute
5. 10% DIEA in DMF for 1 minute
6. Five DMF washes
7. First coupling period
8. Three DMF washes
9. 10% DIEA in DMF for 45 seconds
10. One DMF wash
11. Three DCM washes
- End of First Half -
12. Second coupling period
13. One DMF wash
14. Five DCM washes The first half of the doubling couple cycles are similar to the single couple cycles. The first six processes in the list above are exactly the same as the equivalent processes in a single couple RV cycle. However, there is a longer total coupling time for the double couple cycles. The rboc 1d and rboc 1dr cycles each have a 42-minute (first) coupling period; the rboc 2d and rboc 2dr cycles each have a 26-minute (first) coupling period.

Another difference appears during the washes immediately following the coupling phase. Three DMF washes remove any extra amino acid and then the resin is treated with one more base.

Peptide resins were treated with thiophenol in dimethylformamide to deblock histidine residues (ref. 30).

EXAMPLE 5

Deprotection of the DNP Group Of Histidine From a Peptide-Resin

Suspend the peptide-resin in the reaction vessel in the minimum amount of purified DMF needed to slurry the resin (about 5 ml. per g resin). Add 20 mol of thiophenol (0.102 mL/mmol) for each mole Dnp histidine present. Rock the vessel at ambient temperature for one hour. Thiolysis is rapid and probably complete in fifteen minutes. Wash the resin thoroughly with DMF, water, EtOH, and DCM and dry the peptide-resin. The peptide-resin is then cleaved in the usual way. A small amount of intensely yellow Dnp30 thiophenol is usually absorbed to the resin and is extracted with'the peptide after cleavage. It is easily removed from the peptide in the standard purification procedures.

EXAMPLE 6

Deprotection and Cleavage

The peptides are contacted with HF:anisole:DMS(10:1:1) at $-5°$ to 0C. for 6 minutes.

After removal of the N-terminal t-Boc protecting group, peptides were deblocked and cleaved from the resin with anhydrous hydrogen fluoride.

EXAMPLE 7

Extraction Procedure

After the peptide-resin has reacted in HF at $-5°$ to $0°$ C. for 50 minutes, the HF is easily evaporated with the aid of nitrogen flow within ten to fifteen minutes. To prevent side reactions during this process, it is important to keep the reaction vessel at $-5°$ C. to $0°$ C. After removal of the HF, ether is added to the reaction vessel and the peptide-resin-scavenger mixture is mixed for about 30 seconds. The ether solution is then filtered through a sintered glass funnel. Repeated two more time, this ether wash removes most of the scavengers.

The peptide is extracted from the peptide-resin mixture by stirring the mixture in 30% acetic acid. For those peptides not soluble in 30% acetic acid, a higher concentration of acetic acid is recommended. Typically, for one gram of peptide resin approximately 30 mL of 30% acetic acid is used. The acetic acid extract is filtered through the same sintered glass funnel used to the ether extraction, but into a different filter flask. To ensure complete extraction of the peptide, repeat the extraction procedure using approximately 30 mL of 10% acetic acid (2 times). Dilute the acetic acid solution with water before freeze drying. A more dilute solution of acetic acid in water will remain frozen while a concentrated solution of acetic acid in water may melt during lyophilization.

The solution is then lyophilized to obtain crude peptide.

For peptides containing serine, the N-O shift may occur during HF cleavage. Remaining formyl groups were eliminated by treatment with 1 M ethanolamine in 6 M guanidine-HC1 at $0°$ C. for 5 min.

EXAMPLE 8

Deformylation of Peptide

The formyl (CHO) protecting group of tryptophan is an HF-trifluoromethane sulfonic acid stable species. Deformylation of a peptide synthesized by using TRP (CHO) requires a separate step after strong acid cleavage. Since the deformylation of Trp (CHO) can pose problems to even with the most skilled the following procedure should be strictly followed.

1. Dissolve the peptide containing Trp (CHO) in 6M guanidine HC1 to produce a concentration between 1 and 10 mg/ml.
2. Perform a UV spectral analysis on the dissolved peptide. For a peptide containing Trp (CHO), the 300 nm absorbance is greater than the 280 nm absorbance.
3. Cool the peptide-guanidine solution in an ice bath. Using a magnetic stirring bar, stir the solution until $0°$ is reached.
4. Add enough ethanolamine to the peptide-guanidine solu- solution to produce a final concentration of 1M. (1 mL ethanolamine/16.6 mL peptide-guanidine produces a 1M solution in ethanolamine). After the ethanolamine is added, the pH of the solution should be between 10 and 11.
5. Stir for five minutes at $0°$ C. and then quench by adding concentrated HC1 until the pH reaches 7.
6. Perform a UV spectral analysis on the peptide to ensure complete deformylation of the tryptophan. The 280 nm absorbance is greater for the peptide containing the unprotected Trp than the 300 nm absorbance.
7. The peptide can be desalted on a gel filtration column or dialyzed to remove the guanidine and ethanolamine. Alternatively, the solution is loaded onto a preparative high performance liquid chromatography (HPLC) system for purification.

8. Precautions
   a. Perform a "test" deformylation on 1 mg of peptide.
   b. After dissolving the peptide, chromatograph on an appropriate HPLC system. Column: C-8, Buffer A: 0.1% TFA; Buffer B: 0.1% TFA/60% CH$_3$CN; gradient: 0–100% B in 45 minutes.
   c. After deformylation, rechromatograph to ensure product integrity. The deformylated product should have a slightly shorter retention time.

EXAMPLE 9

Desalting and Purfication

The deformylated crude peptide preparations were desalted on a reverse-phase column (Delta Pak C$_{18}$, 300 A°) using a gradient of acetonitrile in 0.1% trifluoroacetic acid (0–60%, 24 ml/min) followed by cation-exchange chromatography on a TSK 535 CM column (7.5×150 mm) eluted with a NaCl gradient (0–0.5 M) in 20 mM sodium phosphate buffer, pH 6.4.

Final purification was achieved by reverse-phase high performance liquid chromatography (HPLC) on a Vydac column (218TP1022) (0.22×25 cm) with a 25–35% acetonitrile gradient in 0.1% trifluoroacetic acid, flow rate 10 ml/min. The progress of purification was followed using both plasma desorption mass spectrometry (31) and analytical HPLC. The final purity of peptides was greater than 95%. Appropriate peptide composition was verified by quantitative amino-acid analysis.

EXAMPLE 10

Ion - Exchange HPLC

Refer to M. Carlquist et al., (1984) *J. of Chromatography*, Vol. 296, pp. 143–151 for general procedure. A more specific procedure follows:

The instrument for the ion-exchange HPLC consisted of an LKB 2150 HPLC pump, an LKB 2152 HPLC controller, LKB 2040 gradient-mixing valve, an LKB 2154 HPLC injector and an LKB 2151 HPLC variable-wavelength detector connected to an LKB 2210 recorder. The separation was carried out on an LKB UltroPac TSK 535 CM cation-exchanger column (150 −7.5 mm I.D.) Elution was performed with a gradient of sodium chloride (0–0.3 M) in a sodium phosphate buffer, pH 6.4 (1.14 g sodium hydroxide and 22.5 ml 1 M phosphoric acid, and water added to a final volume of 1000 ml), filtered through a Millipore MF-filter (0.22 micro m) and degassed by vacuum. The flow-rate was set at 1 ml/min and the absorbance of the eluent was recorded at 215 nm. Fractions of 2 ml each were collected with an LKB 2112 RediRac fraction collector and evaluated. Purification as obtained on a reverse phase HPLC column.

EXAMPLE 11

PTH/PTHrP Receptor Binding and Adenylate Cyclase Assays

Receptor binding assays were carried out in canine renal plasma membranes and in UMR 106-H5 rat osteosarcoma cells as previously described in detail (Ref. 14,32), using $^{125}$I-labeled PTH(1–34)amide as the radioligand. Binding potency (IC$_{50}$) was quantified as the concentration of unlabeled peptide required for half-maximal displacement of the radioligand. Non-specific binding, defined as residual radioligand binding in the present of a greater than 1, microM unlabeled bPTH(1-34), was subtracted from all binding values. The ratio of specific:non-specific binding of $^{125}$I-PTHrP(1–34)amide average >10:1 and 3:1 in the renal membrane, and UMR 106-H5 assays, respectively. Adenylate cyclase activity was assessed in canine renal membranes by the conversion of [α-32$_p$] ATP to [$^{32}$P] cyclic AMP, essentially as described, except for the addition of 100 micromolar GTP (Ref. 33,34). Adenylate cyclase activity in UMR 106-H5 cells was assessed essentially as described (Ref. 35). In brief, cells were incubated with [3H]adenine 1 micro Ci/ml of serum-free MEM for two hours at 37° C. to label the endogenous ATP pool. Cells were then exposed to 0.4 mM IBMX for 10 min, followed by the appropriate peptide for an additional 10 min at ambient temperature. The cells are then scraped in 20% TCA, and [3H]cyclic AMP is isolated by the column procedure of Salomon et al. (Ref. 36). Potency in the adenylate cyclase assays (Ka) is the concentration of peptide producing half-maximal enzyme activation.

Two novel analogs of human parathyroid hormone 1–34 (HPTH[1–34] were synthesized and tested in several in vitro assay systems (see Tables 5A and 5B). These analogs are [his$^3$]HPTH(1–34) and [leu$^3$] HPTH(1–34). Receptor binding studies indicate that both analogs retain 5–15% of the potency of native [ser$^3$]HPTH(1–34) in binding to PTH receptors in bone and kidney cells. In intact rat (UMR-106) and human (SaOS-2) bone cell lines, the analogs are full agonists with respect to activation of adenylate cyclose. Whereas in intact kidney (CK) cells, [leu$^3$]HPTH(1–34) displays ,25% and [his$^3$]HPTH(1–34)displays <60% of the activity of native-sequence HPTH(1–34) These analogs have markedly diminished adenylate cyclase-stimulating efficacy in membranes derived factor(s) that enhances the ability of occupied PTH receptors to activate adenylate cycase. In the case of these PTH analogs which are only weak agonists in kidney cells, such enhancement allows the expression of full agonist activity in bone cells, at least in vitro. Because this phenomenon is also found to occur in vivo, then it is possible to establish conditions whereby the analogs produce biologic effects on the skeleton (e.g., anabolism) with minimal effects on the kidney.

TABLE 5A

|  | KIDNEY CELLS (CK) | | | BONE CELLS | | | | |
|---|---|---|---|---|---|---|---|---|
|  | | | | Human(SaOS-2) | | Rat(UMR-106) | | |
|  | Potency | | Activity | Potency | Activity | Potency | | Activity |
|  | (B) | (AC) | (AC) | (AC) | (AC) | (B) | (AC) | (AC) |
| hPTH(1–34) | 100 | 100 | 100 | 100 | 100 | 100 | 100 | 100 |
| [his$^3$]hPTH(1–34) | 6 | 13 | 56 | 5 | 100 | 1 | 4 | 100 |
| [leu$^3$]hPTH(1–34) | 22 | 16 | 23 | 11 | 86 | 6 | 13 | 100 |

TABLE 5B

| | BONE CELL MEMBRANES | | RENAL MEMBRANES | | | | |
|---|---|---|---|---|---|---|---|
| | Human SaOS-2 | | Human | | Canine | | |
| | Potency | Activity | Potency | Activity | Potency | | Activity |
| | (AC) | (AC) | (AC) | (AC) | (B) | (AC) | (AC) |
| hPTH(1–34) | 100 | 100 | 100 | 100 | 100 | 100 | 100 |
| [his³]hPTH(1–34) | 11 | 14 | ND | ND | 4 | 1 | 43 |
| [leu³p9 hPTH(1–34) | 8 | 14 | 3 | 35 | 7 | 1 | 47 |

While only a few embodiments of the invention have been shown and described herein, it will become apparent to hose skilled in the art that various modifications and changes can be made in the replacement of the amino acids at 3 and/or 6 and/or 9 positions to produce polypeptide analogs that have agonist or antagonist pharmacological activity without departing from the spirit and scope of the present invention. All such modifications and changes coming within the scope of the appended claims are intended to be carried out thereby.

We claim:

1. A pharmaceutical composition useful in the treatment of disease conditions of bone in a mammal comprising a peptide analog compound of the formula:

$H_2N$-(Ser or Ala)$^1$-Val-B$^3$-Glu-Ile-J$^6$-(Leu or Phe)$^7$-Met-X$^9$-Asn$^{10}$-Leu-Gly-Lys-His—Leu-(Asn or Ser)$^{16}$-Ser-(Met or Leu)$^{18}$-Glu-Arg$^{20}$-Val-Glu-Trp-Leu-Arg-Lys-Lys-Leu-Gln—Asp$^{30}$-Val-His-Asn-Phe$^{34}$-Z (Structure I), or the pharmaceutically acceptable salts thereof, wherein:
   the amino acid B at position 3 is independently selected from L-serine or those other natural or synthetic L-amino acids having a spatial volume comparable to or greater than serine provided that the amino acid B is not glycine or Glu,
   the amino acid J at position 6 is independently selected from L-glutamine or from other natural or synthetic L amino acids,
   the amino acid X at position 9 is independently selected from L-histidine or from other natural or synthetic amino acids,
   with the proviso that when group B is L-serine, and J is L-glutamine, group X is not L-histidine, when group B is L-serine and group X is L-histidine, group J is not L-glutamine, and when group J is L-glutamine and group X is histidine, group B is not L-serine, and
   Z is independently selected from -COOH, -COO-+M wherein +M is selected from pharmaceutically acceptable cations, -(C=O)NH$_2$, or the sequence of amino acids of human, bovine or porcine parathyroid hormone (35–84) or human, bovine or porcine parathyroid hormone-related protein (PTHrP) (35–141); wherein
   said peptide analog compound has a low binding and a low activity in specific soft renal tissue as compared to the reference compound bPTH(1–34), and a high specific bone cell binding and a high activity compared to the activity of said peptide analog compound in soft renal tissue, with the proviso that specific bone cell excludes soft bone marrow cells.

2. The pharmaceutical composition of claim 1 wherein the amino acid at position 1 is serine, the amino acid at position 7 is leucine, the amino acid at position 16 is Asn, the amino acid at position 18 is methionine, and Z is the sequence of amino acids for human PTH (35–84).

3. The pharmaceutical composition of claim 1 wherein the amino acid at position 1 is alanine, the amino acid at position 7 is phenylalanine, the amino acid at position 16 is serine, the amino acid at position 18 is methionine and Z is the sequence of amino acids for bovine PTH (35–84).

4. The pharmaceutical composition of claim 1 wherein structure 1 the amino acid at position 1 is serine, the amino acid at position 7 is leucine, the amino acid at position 16 is serine, the amino acid at position 18 is leucine and Z is the remaining amino acid of porcine PTH (35–84).

5. The pharmaceutical composition of claim 1 wherein Z is -COOH or COO-+M, or -(C=O)NH$_2$.

6. The pharmaceutical composition of claim 5 wherein the amino acid at position 1 is serine, the amino acid at position 7 is leucine, the amino acid at position 16 is Asn, and the amino acid at position 18 is methionine, and Z is COOH or COO-+M or -(C=O)NH$_2$.

7. The pharmaceutical composition of claim 5 wherein the amino acid at position 1 is alanine, the amino acid at position 7 is phenylalanine, the amino acid at position 16 is serine, the amino acid at position 1 8 is leucine, and Z is COOH or COO—+M or —(C=O)NH$_2$.

8. The pharmaceutical composition of claim 5 wherein in structure 1 the amino acid at position 1 is serine, the amino acid at position 7 is leucine, the amino acid at position 16 is serine, the amino acid at position 18 is leucine and Z is COOH or COO—+M or —(C=O)NH$_2$.

9. The pharmaceutical composition of claim 5 wherein J is L-glutamine.

10. The pharmaceutical composition of claim 9 wherein J is independently selected from Leu, Phe, Ala, Glu, Ser or Phe.

11. The pharmaceutical composition of claim 5 wherein J is L-glutamine.

12. The pharmaceutical composition claim 11 wherein B is independently selected from Ala, Phe, Gln, Glu, Lys, His, or Tyr.

13. The pharmaceutical composition of claim 5 wherein B is independently selected from the L-amino acids: Ser, Ala, Phe, Gin, Glu, Lys, His or Tyr.

14. The pharmaceutical composition of claim 5 wherein B is independently selected from the L-amino acids:, Leu, Ala, or Ser.

15. The pharmaceutical composition of claim 1 wherein Z is (C=O)NH$_2$.

16. A pharmaceutical composition comprising a compound of claim 1 or a pharmaceutically acceptable salt thereof in admixture with a pharmacologically acceptable excipient.

17. A pharmaceutical composition useful in the treatment of disease conditions of bone in a mammal comprising a peptide analog compound independently selected from:

H₂N-Ser-Val-Lys-A';
H₂N-Ser-Val-Phe-A';
H₂N-Ser-Val-Leu-A';
H₂N-Ser-Val-Ala-A';
H₂N-Ser-Val-Thr-A';
H₂N-Ser-Val-Cys-A';
H₂N-Ser-Val-Tyr-A';
H₂N-Ser-Val-Asp-A';
H₂N-Ser-Val-Asn-A';
H₂N-Ser-Val-Gln-A';
H₂N-Ser-Val-Lys-A';
H₂N-Ser-Val-Arg-A';
H₂N-Ser-Val-His-A';
H₂N-Ser-Val-Val-A';
H₂N-Ser-Val-Ile-A';
H₂N-Ser-Val-Trp-A';
H₂N-Ser-Val-Met-A';
H₂N-Ser-Val-Pro-A';
H₂N-Ser-Val-Nle-A';
H₂N-Ser-Val-Orn;
H₂N-Ala-Val-Ala-A';
H₂N-Ala-Val-Thr-A';
H₂N-Ala-Val-Cys-A';
H₂N-Ala-Val-Tyr-A';
H₂N-Ala-Val-Asp-A';
H₂N-Ala-Val-Asn-A';
H₂N-Ala-Val-Gln-A';
H₂N-Ala-Val-Lys-A';
H₂N-Ala-Val-Arg-A';
H₂N-Ala-Val-His-A';
H₂N-Ala-Val-Val-A';
H₂N-Ala-Val-Leu-A';
H₂N-Ala-Val-Nle-A';
H₂N-Ala-Val-Pro-A';
H₂N-Ala-Val-Phe-A';
H₂N-Ala-Val-Trp-A';
H₂N-Ala-Val-Met-A';
H₂N-Ala-Val-Ile-A'; or
H₂N-Ala-Val-Orn-A';
where A'is selected from the 4–34 amino acid sequence for human PTH or bovine PTH or their Z=—COOH or —COO—+M, wherein M is a pharmaceutically acceptable cation or —(C=O)NH₂ derivatives, or the 4–84 sequence of hPTH, bPTH, or pPTH or hPTHrP;
H₂N-Ser-Val-Ser-Glu-Ile-Ala-B';
H₂N-Ser-Val-Ser-Glu-Ile-Thr-B';
H₂N-Ser-Val-Ser-Glu-Ile-Cys-B';
H₂N-Ser-Val-Ser-Glu-Ile-Tyr-B';
H₂N-Ser-Val-Ser-Glu-Ile-Asp-B';
H₂N-Ser-Val-Ser-Glu-Ile-Glu-B';
H₂N-Ser-Val-Ser-Glu-Ile-Asn-B';
H₂N-Ser-Val-Ser-Glu-Ile-Ser-B';
H₂N-Ser-Val-Ser-Glu-Ile-Lys-B';
H₂N-Ser-Val-Ser-Glu-Ile-Arg-B';
H₂N-Ser-Val-Ser-Glu-Ile-His-B';
H₂N-Ser-Val-Ser-Glu-Ile-Val-B';
H₂N-Ser-Val-Ser-Glu-Ile-Leu-B';
H₂N-Ser-Val-Ser-Glu-Ile-Ile-B';
H₂N-Ser-Val-Ser-Glu-Ile-Pro-B';
H₂N-Ser-Val-Ser-Glu-Ile-Phe-B';
H₂N-Ser-Val-Ser-Glu-Ile-Trp-B';
H₂N-Ser-Val-Ser-Glu-Ile-Met-B';
H₂N-Ser-Val-Ser-Glu-Ile-Gly-B';
H₂N-Ser-Val-Ser-Glu-Ile-Nle-B';
H₂N-Ser-Val-Ser-Glu-Ile-Orn-B';
H₂N-Ala-Val-Ser-Glu-Ile-Ala-B';
H₂N-Ala-Val-Ser-Glu-Ile-Thr-B';
H₂N-Ala-Val-Ser-Glu-Ile-Cys-B';
H₂N-Ala-Val-Ser-Glu-Ile-Tyr-B';
H₂N-Ala-Val-Ser-Glu-Ile-Asp-B';
H₂N-Ala-Val-Ser-Glu-Ile-Glu-B';
H₂N-Ala-Val-Ser-Glu-Ile-Asn-B';
H₂N-Ala-Val-Ser-Glu-Ile-Ser-B';
H₂N-Ala-Val-Ser-Glu-Ile-Lys-B';
H₂N-Ala-Val-Ser-Glu-Ile-Arg-B';
H₂N-Ala-Val-Ser-Glu-Ile-His-B';
H₂N-Ala-Val-Ser-Glu-Ile-Val-B';
H₂N-Ala-Val-Ser-Glu-Ile-Leu-B';
H₂N-Ala-Val-Ser-Glu-Ile-Ile-B';
H₂N-Ala-Val-Ser-Glu-Ile-Pro-B';
H₂N-Ala-Val-Ser-Glu-Ile-Phe-B';
H₂N-Ala-Val-Ser-Glu-Ile-Trp-B';
H₂N-Ala-Val-Ser-Glu-Ile-Met-B';
H₂N-Ala-Val-Ser-Glu-Ile-Gly-B';
H₂N-Ser-Val-Phe-Glu-Ile-Phe-B';
H₂N-Ser-Val-Phe-Glu-Ile-Nle-B';
H₂N-Ser-Val-Phe-Glu-Ile-Orn-B';
H₂N-Ser-Val-Phe-Glu-Ile-Ser-B';
H₂N-Ser-Val-Tyr-Glu-Ile-Phe-B';
H₂N-Ser-Val-Tyr-Glu-Ile-Ser-B';
H₂N-Ser-Val-Phe-Glu-Ile-Ala-B';
H₂N-Ser-Val-His-Glu-Ile-Ala-B';
H₂N-Ser-Val-Leu-Glu-Ile-Ala-B';
H₂N-Ser-Val-Lys-Glu-Ile-Ala-B';
H₂N-Ser-Val-His-Glu-Ile-Glu-B';
H₂N-Ser-Val-Leu-Glu-Ile-Glu-B';
H₂N-Ser-Val-Lys-Glu-Ile-Glu-B';
H₂N-Ala-Val-Phe-Glu-Ile-Phe-B'
H₂N-Ala-Val-Phe-Glu-Ile-Ser-B';
H₂N-Ala-Val-Val-Glu-Ile-Phe-B';
H₂N-Ala-Val-Tyr-Glu-Ile-Phe-B';
H₂N-Ala-Val-Tyr-Glu-Ile-Ser-B';
H₂N-Ala-Val-Phe-Glu-Ile-Ala-B';
H₂N-Ala-Val-Lys-Glu-Ile-Ala-B';
H₂N-Ala-Val-His-Glu-Ile-Ala-B';
H₂N-Ser-Val-His-Glu-Ile-Ala-B'; or
H₂N-Ser-Val-Leu-Glu-Ile-Ala-B';
wherein Group B'is selected from the remainder of the remaining peptides of 7–34 active unit of hPTH, bPTH, or pPTH, or their Z=COOH or COO—+M or —(C=O)NH₂derivatives, or the 7–84 sequence of hPTH or bPTH or hPTrH;
H₂N-Ser-Val-Phe-Glu-Ile-Gln-Leu-Met-His-D';
H₂N-Ser-Val-Phe-Glu-Ile-Ser-Leu-Met-His-D';

H₂N-Ser-Val-Ser-Glu-Ile-Phe-Leu-Met-His-D';
H₂N-Ser-Val-Ser-Glu-Ile-Ser-Leu-Met-His-D';
H₂N-Ser-Val-Tyr-Glu-Ile-Gln-Leu-Met-His-D';
H₂N-Ser-Val-Tyr-Glu-Ile-Ser-Leu-Met-His-D';
H₂N-Ser-Val-Tyr-Glu-Ile-Phe-Leu-Met-His-D';
H₂N-Ser-Val-Phe-Glu-Ile-Phe-Leu-Met-His-D';
H₂N-Ser-Val-Tyr-Glu-Ile-Nle-Leu-Met-His-D'; or
H₂N-Ser-Val-Phe-Glu-Ile-Orn-Leu-Met-His-D';
H₂N-Ser-Val-Ser-Glu-Ile-Gln-Leu-Met-Ala-D';
H₂N-Ser-Val-Ser-Glu-Ile-Gln-Leu-Met-Ser-D';
H₂N-Ser-Val-Ser-Glu-Ile-Gln-Leu-Met-Leu-D';
H₂N-Ser-Val-Ser-Glu-Ile-Gin-Leu-Met-Phe-D';
H₂N-Ser-Val-Ser-Glu-Ile-Gln-Leu-Met-Tyr-D';
H₂N-Ser-Val-Ser-Glu-Ile-Gin-Leu-Met-Glu-D';
H₂N-Ser-Val-Ser-Glu-Ile-Gln-Leu-Met-Lys-D';
H₂N-Ser-Val-Ser-Glu-Ile-Gln-Leu-Met-Gln-D';
H₂N-Ser-Val-Ser-Glu-Ile-Gln-Leu-Met-Nle-D';
H₂N-Ala-Val-Ser-Glu-Ile-Gln-Phe-Met-Ala-D';
H₂N-Ala-Val-Ser-Glu-Ile-Gln-Phe-Met-Ser-D';
H₂N-Ala-Val-Ser-Glu-Ile-Gln-Phe-Met-Leu-D';
H₂N-Ala-Val-Ser-Glu-Ile-Gln-Phe-Met-Phe-D';
H₂N-Ala-Val-Ser-Glu-Ile-Gln-Phe-Met-Tyr-D';
H₂N-Ala-Val-Ser-Glu-Ile-Gln-Phe-Met-Glu-D';
H₂N-Ala-Val-Ser-Glu-Ile-Gln-Phe-Met-Lys-D';
H₂N-Ala-Val-Ser-Glu-Ile-Gln-Phe-Met-Gln-D';
H₂N-Ala-Val-Ser-Glu-Ile-Gln-Phe-Met-Nle-D'; or
H₂N-Ala-Val-Ser-Glu-Ile-Gln-Phe-Met-Orn-D';
H₂N-Ala-Val-Phe-Glu-Ile-Gln-Phe-Met-His-D';
H₂N-Ala-Val-Phe-Glu-Ile-Ser-Phe-Met-His-D';
H₂N-Ala-Val-Ser-Glu-Ile-Phe-Phe-Met-His-D';
H₂N-Ala-Val-Ser-Glu-Ile-Ser-Phe-Met-His-D';
H₂N-Ala-Val-Tyr-Glu-Ile-Gln-Phe-Met-His-D';
H₂N-Ala-Val-Tyr-Glu-Ile-Ser-Phe-Met-His-D';
H₂N-Ala-Val-Phe-Glu-Ile-Phe-Phe-Met-His-D';
H₂N-Ala-Val-Tyr-Glu-Ile-Phe-Phe-Met-His-D'; or
H₂N-Ala-Val-Nle-Glu-Ile-Phe-Phe-Met-His-D' or the pharmaceutically acceptable salts thereof, wherein D'is selected from the 10–34 amino acid sequence for human or bovine PTH or their Z=—COOH or COO—+M or —(C=O)NH₂ derivatives, or the remaining 10–84 sequence of pPTH, bPTH, pPTH or hPTHrP in combination with a pharmaceutically acceptable excipient; wherein said peptide analog compound has a low binding and a low activity in specific soft renal tissue as compared to the reference compound bPTH (1–34), and a high specific bone cell binding and a high activity compared to the activity of said peptide analog compound in soft renal tissue, with the proviso that bone cells excludes soft bone marrow cells.

18. The pharmaceutical composition of claim 17 wherein A', B'or D'is hPTH (1–34) terminating in —COOH.

19. The pharmaceutical composition of claim 17 wherein A', B'or D'is hPTH (1–34) terminating in COO—+M, wherein M is selected from sodium, potassium, calcium or barium.

20. The pharmaceutical composition of claim 17 wherein the amino acids at position 1 and 3 are L-serine and A', B' or D'is hPTH (1–34) terminating in Z=—COOH or COO—+M or —(C=O) NH₂.

21. The pharmaceutical composition of claim 17 wherein the amino acid at position 1 is L-alanine, B is serine, A', B'or D' is bPTH (4–34) terminating in Z=—COOH or COO—=M or -(C=O) NH₂.

22. The pharmaceutical composition of claim 17 wherein the amino acid at position 1 is L-serine, and the amino acid at position 3 is not L-serine and A', B' or D' is hPTH (1–34) terminating in Z=-COOH or COO—+M or —(C=O) NH₂.

23. The pharmaceutical composition of claim 17 wherein the amino acid at position 1 is L-alanine, and the amino acid at position 3 is not L-serine serine and are A', B' or D' is bPTH (1–34) terminating in Z=—COOH or COO—+M or —(C=O) NH₂.

24. The pharmaceutical composition of claim 17 wherein the amino acid at position 1 is serine, the amino acid at position 3 is serine, the amino acid at position 6 is not L-glutamine and A', B' or D' is hPTH (1–34) terminating in Z=—COOH or COO—+M or —(C=O) NH₂.

25. The pharmaceutical composition of claim 17 wherein the amino acids at positions 1 and 3 are L-serine, the amino acid at position 6 is L-glutamine and the amino acid at position 9 is not L-histidine and group D' is hPTH(10–34) terminating in Z=—COOH or COO—+M or —(C=O) NH₂.

26. The pharmaceutical composition of claim 17 wherein Z is (C=O)NH₂.

27. A method of treatment of a mammal in need of therapeutic treatment for a disease of the bone, which method comprises administration of a therapeutically effective amount of the pharmaceutical composition of claim 15 or the pharmaceutically acceptable salt thereof in admixture with a pharmaceutically acceptable excipient.

28. The method of claim 27 which comprises administration of a therapeutically effective amount of structure I by oral, parenteral, subcutaneous, intramuscular, intravenous, vaginal, rectal, buccal, sublingual or intranasal means.

29. The method of claim 28 wherein the compound is used to treat osteoporosis, hypercalcemia or hyperparathyroid conditions in a human being.

* * * * *